(12) United States Patent
Maurer

(10) Patent No.: US 8,877,458 B2
(45) Date of Patent: *Nov. 4, 2014

(54) METHOD OF DETECTING BACTERIAL CONTAMINATION USING DYNAMIC LIGHT SCATTERING

(75) Inventor: Elisabeth Maurer, Vancouver (CA)

(73) Assignee: Canadian Blood Services, Ottawa, Ontario (CA)

( * ) Notice: Subject to any disclaimer, the term of this patent is extended or adjusted under 35 U.S.C. 154(b) by 441 days.

This patent is subject to a terminal disclaimer.

(21) Appl. No.: 12/525,467

(22) PCT Filed: Feb. 1, 2008

(86) PCT No.: PCT/CA2008/000212
§ 371 (c)(1),
(2), (4) Date: Jul. 31, 2009

(87) PCT Pub. No.: WO2008/092272
PCT Pub. Date: Aug. 7, 2008

(65) Prior Publication Data
US 2010/0136611 A1 Jun. 3, 2010

Related U.S. Application Data

(60) Provisional application No. 60/887,903, filed on Feb. 2, 2007.

(51) Int. Cl.
*C12Q 1/04* (2006.01)
*G01N 15/02* (2006.01)
*G01N 15/00* (2006.01)

(52) U.S. Cl.
CPC .............. *C12Q 1/04* (2013.01); *G01N 15/0211* (2013.01); *G01N 2015/0222* (2013.01); *G01N 2015/03* (2013.01)
USPC .................... 435/34; 435/29; 435/39; 356/39; 356/336; 356/337; 73/61.71

(58) Field of Classification Search
None
See application file for complete search history.

(56) References Cited

U.S. PATENT DOCUMENTS

| | | | |
|---|---|---|---|
| 4,080,264 | A | 3/1978 | Cohen et al. |
| 4,781,460 | A * | 11/1988 | Bott ............................... 356/336 |
| 4,828,976 | A * | 5/1989 | Murphy ............................. 435/2 |
| 5,496,301 | A | 3/1996 | Hlavinka et al. |
| 5,815,611 | A | 9/1998 | Dhadwal |
| 5,817,518 | A | 10/1998 | Li et al. |
| 5,973,779 | A | 10/1999 | Ansari et al. |
| 6,043,871 | A | 3/2000 | Solen et al. |
| 2001/0024800 | A1* | 9/2001 | Garcia-Rubio et al. ....... 435/7.21 |
| 2002/0180972 | A1* | 12/2002 | Ansari et al. .................. 356/336 |
| 2004/0100630 | A1* | 5/2004 | Yamaguchi et al. ........... 356/336 |
| 2005/0250095 | A1* | 11/2005 | Gabriel .............................. 435/5 |
| 2006/0046280 | A1 | 3/2006 | Maurer-Spurej |

FOREIGN PATENT DOCUMENTS

| WO | 9014588 | 11/1990 |
|---|---|---|
| WO | 02/16951 A2 | 2/2002 |

OTHER PUBLICATIONS

Frojmovi, MM et al. Human platelet size, shape, and related functions in health and disease. Physiological Rev. 1982. 62: 185-261.*
Katz, A et al. Bacteria size determination by elastic light scattering. IEEE Journal of Selected Topics in Quantum Electronics. 2003. 9(2): 277-287.*
Portable dynamic light scattering instrument and method for the measurement of blood platelet suspensions; Maurer-Spurej, Elisabeth, et al.; Physics in Medicine and Biology, 51 (Jul. 20, 2006) pp. 3747-3758.
Platelet Microparticles: a wide-angle perspective; Horstman, Lawrence L, et al.; Critical Reviews in Oncology/Hematology; 30, (1999) pp. 111-142.
Abrams, C.S., et al., Blood. 1990. 75(1), 128-138.
Cram, S.L. Methods in Cell Science. 2002, 24(1-3), 1-9.
Hoffmeister, K.M., et al. Cell. 2003.112(1), 87-97.
Rock, G. et al. Transfusion and Apheresis Science. 2006. 35, 145-149.
Fratantoni et al., J. Lab. Clin. Med., vol. 103 (4), pp. 620-631 (1984).
David et al., Coll. Surfaces B.: Biointerfaces, vol. 6 pp. 101-114 (1996).
Hubbell et al., Thromb Haemost, vol. 65, pp. 601-607, (1991).
Maurer-Spurej et al., Lab. Invest., vol. 81 (4), pp. 581-592 (2001).
Spurej et al., Experientia, vol. 48, pp. 71-79 (1992).
D. Zelmanovic et al., Vet. Clin. Pathol., vol. 27 (1), pp. 2-9 (1998).
Eto et al., Cardiovascular Research, vol. 40 (1), pp. 223-229 (1998).
Tomida et al., Thromb. Res., vol. 92, pp. 221-228 (1998).
Yabusaki et al., Langmuir, vol. 18, pp. 39-45 (2002).
J. Seghatchian et al., "Transfus. Sci.", vol. 18, No. 1, pp. 27-32 (1997).
Devine, D. V., et al., "Platelet Aggregation is Not Initiated by Platelet Shape Change", Laboratory Investigation, Nov. 2001, vol. 81, pp. 1517-1525.
Maurer-Spurej, E. et al., "Activation Studies on Human Platelets Using Electrophoretic and quasi-elastic light scattering", Progress in Colloid & Polymer Science, 1990, -vol. 81: 151-155.
Devine D. V., et al., SP254, "Platelet Shape Change is Not Required for Aggregation-Initail Decrease of Light Transmision in Platelet Aggregometry Indicates Platelet Micro-Aggregation But Not Shape Change", Transfussion, 2000—vol. 40, Supplement.
Maurer-Spurej, E., SP145, "Novel Dynamic Light Sctattering Method for the Dertermination of Platelet Quality and Viability", Canadian Blood Services, Canada, Transfusion, 2004—vol. 44, Supplement.
International Search Report PCT/CA2008/000212; Dated May 9, 2008.

* cited by examiner

Primary Examiner — Allison Fox
Assistant Examiner — Susan E Fernandez
(74) Attorney, Agent, or Firm — Hancock Hughey LLP

(57) ABSTRACT

Methods of detecting bacterial contamination in a platelet concentrate are performed using a dynamic light scattering (DLS) instrument and a sample holder. A sample of platelet concentrate can be held vertically or horizontally in a capillary in the sample holder. Alternatively, novel platelet storage bags modified to include an optically translucent window can be held within another variant of the sample holder. Still alternatively, platelet storage bags having one or more tubes detachably appended to the bag can be used. A sample is drawn off into an appended tube for placement directly into the sample holder. This method provides a number of related, non-invasive techniques for detecting whether bacteria has contaminated a platelet concentrate. Contamination indicators include a population of particles different from platelets, microparticles or proteins, bad-quality platelets, i.e. low DLS score, and very high or very low scattering intensity.

10 Claims, 19 Drawing Sheets

DLS Score = 23

DLS Score = 8

3 day12 hep 20_1.dat Intensity Distrib, (nm)

❖ Distribution analysis

Fitting range         : [100; 530] channels
Number of Intervals   : 200
Boundaries            : [0.002; 2.6e+8]
Resolution            : 1.000

| Peak Num | Area | Mean | Position | STD |
|---|---|---|---|---|
| 1 | 0.007 | 0.273 | 0.274 | 0.013 |
| 2 | 0.993 | 1439. | 1443. | 160.7 |

| Peak Num | Area | Mean | Position | STD |
|---|---|---|---|---|
| 1 | 1.000 | 468.2 | 456.3 | 60.42 |

Intensity Flag

DLS Score = 17

DLS Score = 13 Intensity Flag

DLS score = 7

Figure 11

| Sample | DLS score (unacceptable when < 12) | BacT/ALERT Time until positive [h] | Phase contrast | Gram stain |
|---|---|---|---|---|
| BC #1 | 25 | neg | | |
| Contaminated | 6 | 6 | | 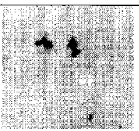 |
| Aph #2 Day 1 | 17 | neg | | |
| Day 7 | 13[&] | False neg | 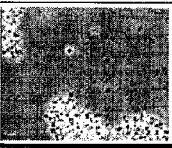 | |
| Aph #3 Day 1 | 23 | neg | | |
| Day 7 | 8 | False neg | 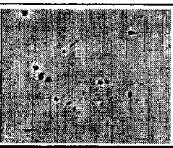 | |
| Aph #7 Day 1 | 22 | neg | | |
| Day 7 | -1 | False neg | 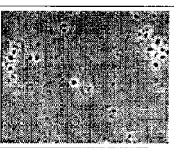 | |
| Aph #43 | 1 | False neg |  | |
| PT 01-001 | 8 | nd | |  |
| Platelets + SE 200 cfu/mL | 17 | 15.36 | | |
| Platelets + SE 4.5 x 10$^6$ cfu/mL | 11[&] | nd | |  |
| Beads 1 micron | -9 | nd | | |

\* SE = *Staphylococcus epidermidis*
\*\* DLS = dynamic light scattering
nd = not determined     [&] High scattering intensity flag

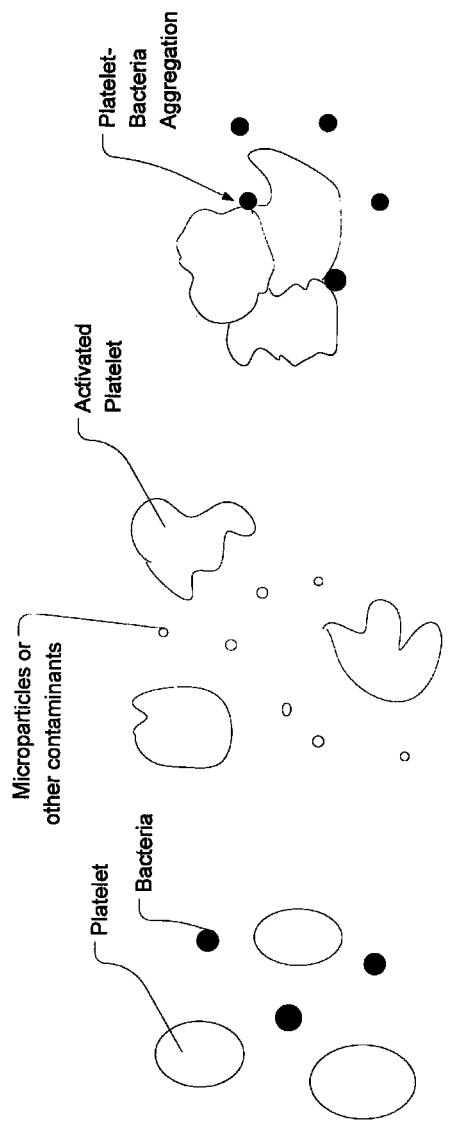

METHOD OF DETECTING BACTERIAL CONTAMINATION USING DYNAMIC LIGHT SCATTERING

TECHNICAL FIELD

This application relates in general to dynamic light scattering and, more particularly, to the detection of bacterial contamination using dynamic light scattering.

BACKGROUND OF THE INVENTION

Bacterial contamination of platelet concentrates represents a risk of morbidity and mortality in transfusions. Approximately 1 in 2000 to 1 in 5000 platelet concentrates are believed to be bacterially contaminated. In 2004, the Food and Drug Administration (FDA) recommended bacterial testing of all platelet units. The American Association of Blood Banks (AABB) standard 5.1.5.1 requires bacterial testing on every platelet unit (thus requiring 100% quality control). Canada produces approximately 300,000 platelet concentrates annually. In the United States, about 4 million platelet products are produced every year. Even testing of pooled products means millions of tests annually in North America alone. Furthermore, the current proposal in the industry to extend platelet storage from 5 to 7 days will require bacterial testing.

Currently, platelet concentrate units are only tested for bacteria at the end of the manufacturing process (i.e. at Day 0 or Day 1 of storage). This single test involves sampling of 4-10 ml from the platelet unit into a growth bottle. After 24-48 hours of culture, aerobic bacteria are measured by the amount of $CO_2$ production. Facultative/anaerobic bacteria are measured by the amount of $O_2$ production. Two different culture bottles are required for the two different metabolites. The only approved instrument known to Applicant is the BacT/ALERT® from bioMérieux (http://www.biomerieux-usa.com). However, one shortcoming of using this instrument is that the platelet product cannot be released for 1-2 days until the BacT/ALERT® results are available. Because of the sampling requirement, this is a one-time test. As contamination levels are usually low at the beginning, the BacT/ALERT® yields a high rate of false-negative results. In other words, samples that are thought to be bacteria-free may actually turn out later to be contaminated because the BacT/ALERT® lacks the sensitivity to detect low levels of bacteria in the sample at an early stage.

In view of the shortcomings of the prior art, an improved method for detecting bacterial contamination in a sample remains highly desirable.

SUMMARY OF THE INVENTION

This novel method of detecting bacterial contamination in a platelet concentrate involves placing a sample of the platelet concentrate into a dynamic light scattering (DLS) instrument. A quantity of bacteria in the sample is then determined from the relative intensity of the scattered light relative to the incident light for a particle size corresponding to a particular species of bacteria. In other words, from a size distribution showing peaks of intensity at certain particle sizes, it is possible to discriminate the platelets, microparticles, proteins and bacteria based on previously obtained empirical data, i.e. by expected size ranges within which certain types of particles will be found. In addition, bacterial toxins affect platelets, microparticles and proteins. The changes caused by bacterial toxins can be detected by dynamic light scattering even in the absence of live bacteria or in cases where the size of bacteria is similar to that of platelets or microparticles. Further, multiplication of bacteria significantly increases the scattering intensity and aggregation of platelets and bacteria significantly decreases the scattering intensity. Abnormally high or low scattering intensity, compared to a known standard of latex beads, will flag the platelet concentrate as bacterially contaminated. Samples of platelet concentrate can be drawn into one or more tubes detachably appended to a platelet storage bag. Each tube can then be placed directly into a sample holder where it is held preferably (but not necessarily) upright (and possibly heated or cooled) to obtain highly sensitive DLS measurements to discriminate the bacteria content from the platelets, microparticles and proteins also found in the sample and/or measure the toxic effect of bacteria on platelets, microparticles and proteins. Alternatively, a platelet bag with an optical window can be placed onto a modified, horizontal sample holder to measure dynamic light scattering at a very large scattering angle. In certain cases, the scattering angle would be in the range of 120-170 degrees. In other words, backscattering can be used to collect DLS data from a platelet sample contained within a platelet bag that has been modified to have an optical window on its surface. These related methods provide a non-invasive, fast, highly sensitive, reliable and inexpensive technique for detecting whether bacteria has contaminated a platelet concentrate.

In general, there are three basic indicators for bacterial contamination:
1. A population of particles different from platelets, microparticles or proteins;
2. Bad quality platelets, i.e. low DLS score because of bacterial toxins or other direct effects of bacteria on platelets; and
3. Very high or very low scattering intensity (i.e., if the intensity is doubled from what is expected of a platelet concentrate, the unit is flagged because the added scattering particles must be contaminants whereas, on the other hand, when platelets and bacteria aggregate they will settle out of the observation volume and the intensity will be very low.

For each of these three indicators, three different DLS instrument setups can be used. In a first setup, the DLS instrument uses a sample holder that holds a capillary (or equivalent), typically in a substantially upright (vertical) posture or a substantially horizontal posture (but which, in theory, could be oriented at any angle). DLS measurements can be obtained on the sample to determine whether the sample is contaminated. In a second setup, the same DLS instrument (including the same sample holder) is used but rather than transferring the sample into a standard capillary, the sample is drawn directly from the platelet storage bag into a detachable tube that is appended to the bag. This can be done by squeezing a filling bulb at the end of the tube to suction a volume of platelet concentrate into the tube. DLS measurements can then be made on the sample contained within the detachable tube. In a third setup, rather than taking DLS measurements on a sample in a thin tube or capillary, the DLS measurements are taken directly on the platelet concentrate contained within the platelet storage bag. The platelet storage bag is held between clamping members of a modified sample holder such that DLS measurements can be taken through an optically translucent window formed in a wall of the bag. Unlike the first and second setups where the capillary or tube can be subjected to temperature cycling, the third setup does not allow for any such temperature variation.

Accordingly, one aspect of the present invention is a method for detecting bacteria in a sample that entails placing the sample in a dynamic light scattering (DLS) instrument, collecting DLS measurements from the sample, and determining whether bacteria are present in the sample based on the DLS measurements from the sample.

Another aspect of the present invention is a platelet storage bag for use with a DLS instrument capable of detecting bacterial contamination in a platelet concentrate, the bag comprising at least one tube appended in selective fluid communication with the bag, the tube being adapted to be received within the DLS instrument to enable DLS measurements to be taken on the sample from which it can be determined whether the sample is contaminated with bacteria. Alternatively, the platelet storage bag has an optical window. This window is aligned with the optical fibers by means of a modified sample holder such as, for example, a modified horizontal sample holder shown in FIG. 5B. Through the optical window, DLS measurements can be made on the bag content, i.e. the sample of platelets, to determine whether the platelets in the bag are contaminated with bacteria.

Yet another aspect of the present invention is a system for detecting bacterial contamination of a platelet concentrate. The system includes a platelet bag with a sample tube appended to the bag to enable a sample of platelet concentrate to be drawn into the tube, and a sample holder for holding the tube to perform DLS measurements on the sample in order to detect whether the platelet concentrate has been bacterially contaminated. In its preferred embodiment, the sample holder has a base having an upright backing member and a movable clamping member that moves relative to the backing member between an open, retracted position, in which the clamping member no longer contacts the tube, and a closed, holding position, in which the clamping member presses against the tube to lightly clamp the tube between the clamping member and the backing member, wherein the backing member and clamping member each comprises at least one optical access slot enabling scattered light to be collected at one of a plurality of oblique angles relative to a beam of incident light. The system further includes a light source for directing the beam of light at the sample through one of the optical access slots, a light collector for collecting light scattered by the sample through another one of the optical access slots, and a correlating means for correlating collected scattered light to particle size to determine a quantity of bacteria in the sample.

In this system, the sample holder may also include heating/cooling elements for varying the temperature of the platelet sample so that temperature-dependent measurements can be made at specific temperatures (e.g. 37° C.). For example, because bacteria multiply over time, causing their signal to increase (depending on the species), it is possible to more accurately discriminate the bacteria by varying the temperature of the sample.

In an alternative embodiment, the sample holder has substantially horizontal clamping plates. In this embodiment, the bottom (lower) clamping plate is fixed while the top (upper) clamping plate is vertically movable so that the sample holder can be "opened vertically" to enable a whole platelet bag to be positioned between the horizontal clamping plates (which can then be closed, i.e. by lowering the upper clamping plate onto the platelet bag to provide alignment of the optical window relative to the optical fibers for the incident and scattered light.

Yet a further aspect of the present invention is a system for detecting bacterial contamination of a platelet concentrate, the system including a platelet storage bag containing a platelet concentrate, the bag having an optically translucent window in a wall of the bag through which light can pass; a sample holder for holding the bag between a stationary clamping member and a movable clamping member such that the optically translucent window aligns with an optical access slot in the stationary clamping member; a light source for directing a beam of light through the optical access slot of the stationary clamping member and through the optically translucent window of the platelet storage bag; a light collector for collecting backscattered light exiting through the optically translucent window of the bag and through the optical access slot of the stationary clamping member; and a correlating means for correlating collected backscattered light to particle size to determine whether the platelet concentrate in the bag is contaminated.

Yet a further aspect of the present invention is a method of detecting bacterial contamination in a platelet sample. The method includes steps of obtaining DLS measurements from the platelet sample, determining whether a DLS score that is computed based on the DLS measurements is below a predetermined threshold, and identifying the platelet sample as being bacterially contaminated when the DLS score is below the predetermined threshold.

Yet a further aspect of the present invention is a method of detecting bacterial contamination in a platelet sample. The method includes steps of obtaining DLS measurements from the platelet sample; determining whether an intensity of scattered light from the DLS measurements is below a first predetermined intensity threshold or above a second predetermined intensity threshold; and identifying the platelet sample as being bacterially contaminated when the DLS score is below the first predetermined intensity threshold or above the second predetermined intensity threshold.

Yet a further aspect of the present invention is a method of detecting bacterial contamination in a sample of platelets. The method includes steps of obtaining DLS measurements on the sample of platelets by illuminating the sample with incident light and by collecting the scattered light; determining a particle size distribution based on the scattered light; identifying a cluster of particles on the particle size distribution that is distinct from a cluster of particles known to correspond to platelets; and determining whether the sample is bacterially contaminated by the cluster of particles that are distinct from the cluster of particles corresponding to platelets.

BRIEF DESCRIPTION OF THE DRAWINGS

Further features and advantages of the present invention will become apparent from the following detailed description, taken in combination with the appended drawings, in which:

FIG. 11 is a table comparing Applicant's Dynamic Light Scattering-Platelet Monitor ("DLS-PM") implementing the present invention with a prior-art instrument, the BacT/ALERT to report a sample as being positive for bacterial contamination, and microscopic images (phase contrast or Gram stain);

FIG. 12A is a schematic depiction of a sample of platelets contaminated with bacteria that can be directly measured as a population of particles having a size that is different from that of platelets;

FIG. 12B is a schematic depiction of a sample of activated platelets having a low DLS score due to bacterial toxins or other direct effects of bacteria on platelets, leading to the production of microparticles or other contaminants; and FIG. 12C is a schematic depiction of how very high (or very low) intensity can be indicative of platelet aggregation or, alternatively, high particle count.

DETAILED DESCRIPTION OF EMBODIMENTS

Various embodiments and aspects of the present invention will now be described, including a novel DLS bacteria-detection system, a novel platelet storage bag, and a novel method of using DLS to detect bacteria. While the method, bag and bacteria-detection system are preferably used together, the method may be performed using a different DLS system and/or without using the novel platelet storage bag. However, if a different DLS system is to be used, needle sampling is required (with all the associated disadvantages) or the test would have to be done on a post-production sample (as is done using the prior-art BacT/ALERT system.)

DLS Bacteria Detection System

Figure 1A:
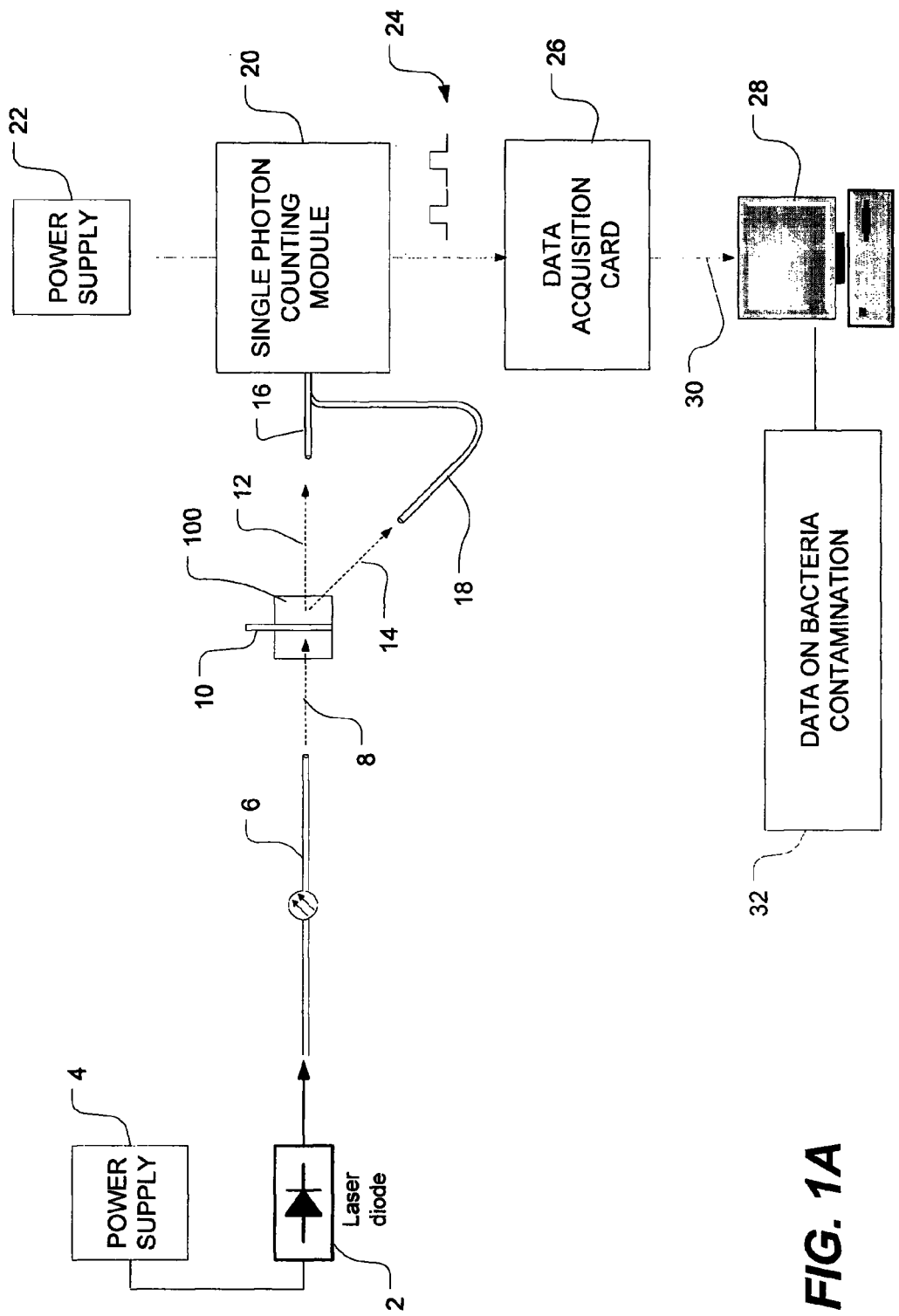
FIG. 1A is a schematic view of a DLS bacteria-detection system in accordance with a first embodiment of the present invention in which a capillary (or tube) containing a platelet sample is held substantially vertically for analysis.

FIG. 1A is a schematic view of a bacteria detection system using dynamic light scattering (DLS), which is also known as quasi-elastic light scattering (QELS). As shown in FIG. 1A, the system has a light source such as, for example, a laser diode 2 which is powered by a power source, as is well known in the art. The laser diode 2 generates and emits a beam of laser light into a length of optical fiber 6. The laser preferably generates light at 635 nm although other wavelengths could be used, as would be appreciated by those of ordinary skill in the art. As is also known in the art, the intensity of the laser beam can be adjusted using an adjustable neutral density filter (or by using an attenuator in the fiber) which allows the laser to be operated at maximum power while curtailing the intensity of the incident light. This reduces multiple scattering and other undesirable optical effects that arise when the intensity of the incident light is too high. The optical fiber is preferably a single-mode, polarization-maintaining optical fiber which, as is well known in the art, prevents the polarization from drifting when the light propagates through the optical fiber or, alternatively, a multimode fiber can be utilized. As is known in optics, polarization-maintaining fibers can be made using fibers of noncircular cross-section or by making the propagation medium of the fibers anisotropic such as, for example, by stressing the fibers in a specific direction.

Figure 1B:
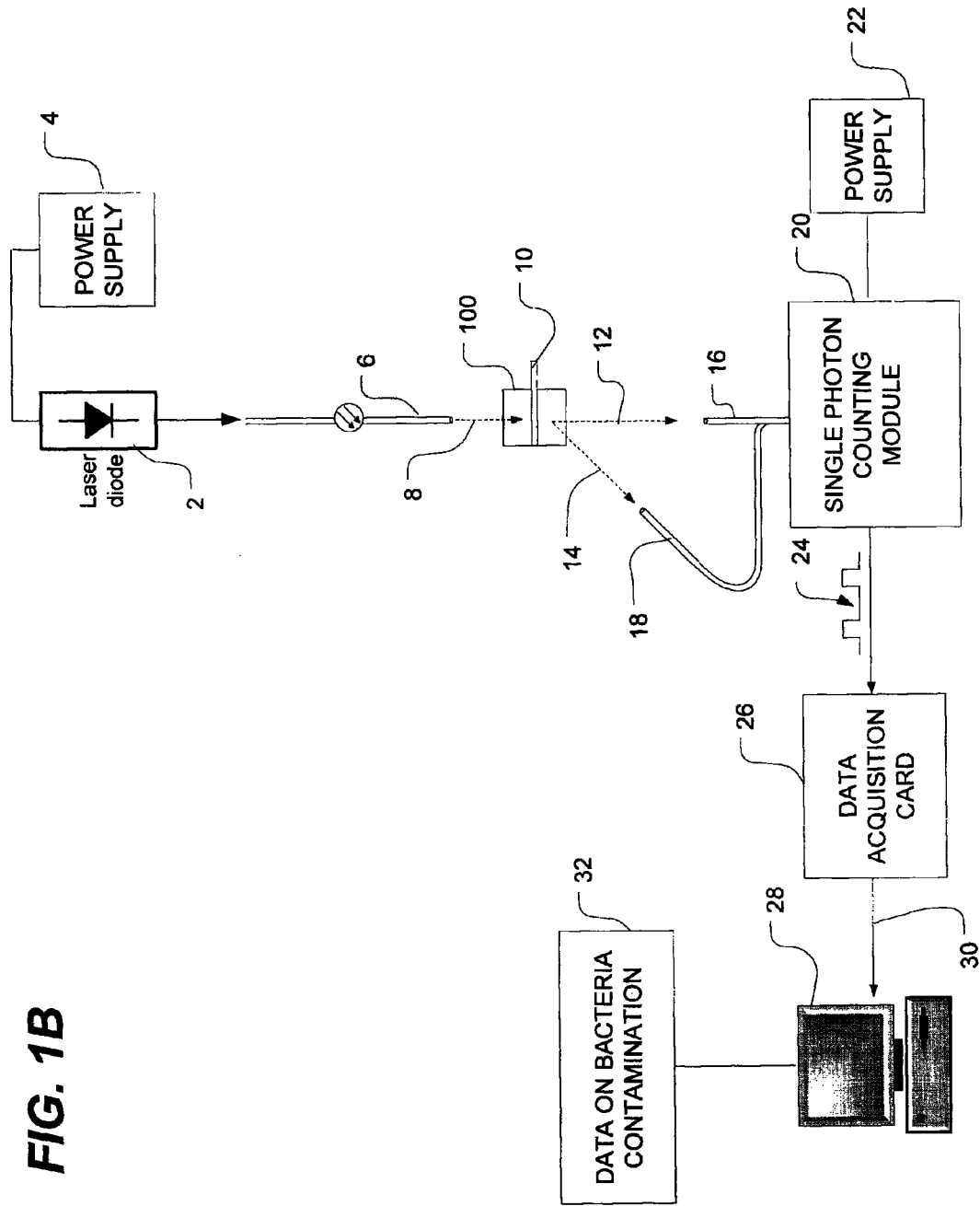
FIG. 1B is a schematic view of a DLS bacteria-detection system in accordance with a second embodiment of the present invention in which a capillary (or tube) containing a platelet sample is held substantially horizontally for analysis.
Figure 1C:
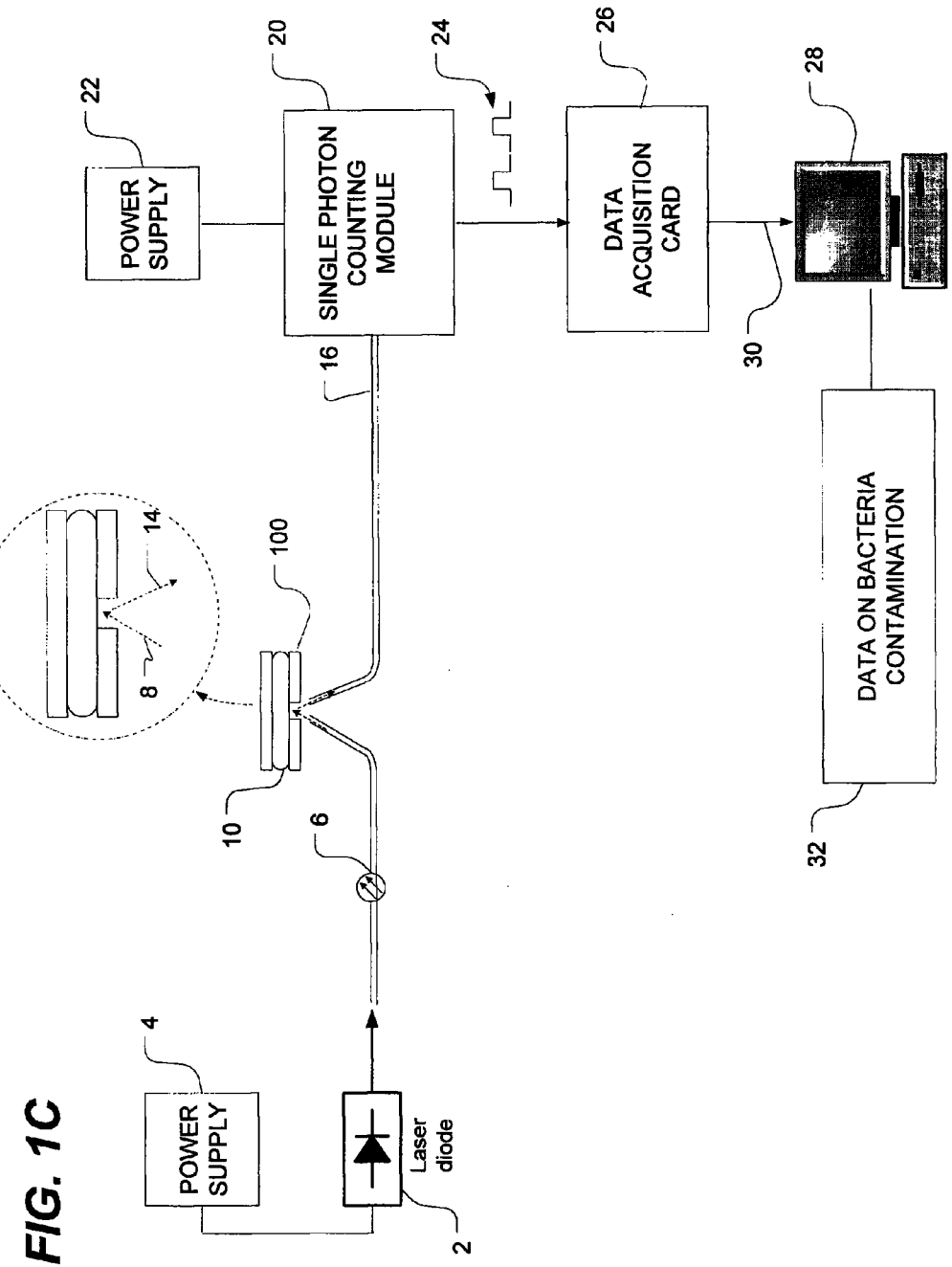
FIG. 1C is a schematic view of a DLS bacteria-detection system in accordance with a third embodiment of the present invention in which a modified platelet bag having an optical access window is held directly between clamping plates of the sample holder.

As shown in FIG. 1A, the polarized laser light emerges from the single-mode, polarization-maintaining optical fiber 6 and travels a short distance through the air (although it should be expressly understood that the distances shown in FIG. 1A are not meant to be representative or proportional to actual distances). This incident light impinges on a fluid sample (e.g. platelets in solution, whole blood, or other colloids or colloidal dispersions) contained within a transparent or translucent tube or container 10 (e.g. a capillary, cuvette, or like structure) held by a sample holder 100 in accordance with embodiments of the present invention. The sample holder 100 will be described in greater detail below with reference to FIGS. 2-4. The sample holder 100 can also be disposed as shown in FIG. 1B, in which the capillary holding the platelet sample is substantially horizontal. This sample holder could open vertically to receive a sample container horizontally (FIG. 1B). Alternatively, as shown in FIG. 1C, the sample holder 100 can receive or accommodate a whole platelet bag that has been modified to include an optical access window. The sample holder 100 depicted in FIG. 1C for accommodating a whole platelet storage bag would, unlike the sample holders 100 shown in FIGS. 1A and 1B for capillaries, only operate at room temperature (22±2° C.). This sample holder can be made larger, with mounting pins for whole platelet bags and an opening for optical access of the incident light and collection of the backscattered light as illustrated in FIG. 1C.

As shown in FIG. 1A, the incident light scatters when photons strike particles suspended in the solution. The scattered light 12, 14 scatters in various directions away from the fluid sample. A portion of this scattered light is collected by light collectors 16, 18, which are preferably optical fibers connected to a single-photon counting module 20 powered by a power supply 22. In a preferred embodiment, the single-photon counting module 20 generates TTL pulses (transistor-transistor logic pulses) 24 and transmits these TTL pulses 24 to a data acquisition card 26. The data acquisition card 26 digitizes the TTL pulses and communicates the "raw data" to a software correlator running on a laptop or other computer 28. This raw data is communicated via a universal serial bus (USB) 30 or other data bus or connector. Alternatively, the data acquisition card 26 can be installed within the computer 28. Together, the data acquisition card 26, computer 28 and software correlator constitute a "correlating means", as this expression is used in the present specification. Alternatively, the correlating means could utilize a hardware correlator (e.g. a multi-tau correlator) instead of the data acquisition card. The hardware correlator would generate and communicate a correlation function to the computer, although the data acquisition card and software correlator are preferred as it has been found to be more versatile and cost effective. Particle size (i.e. hydrodynamic radius) is obtained by correlating the observed speckle pattern that arises due to Brownian motion and solving the Stokes-Einstein equation, which relates the particle size to the measured diffusion constant, as is known in the art.

Figure 2:
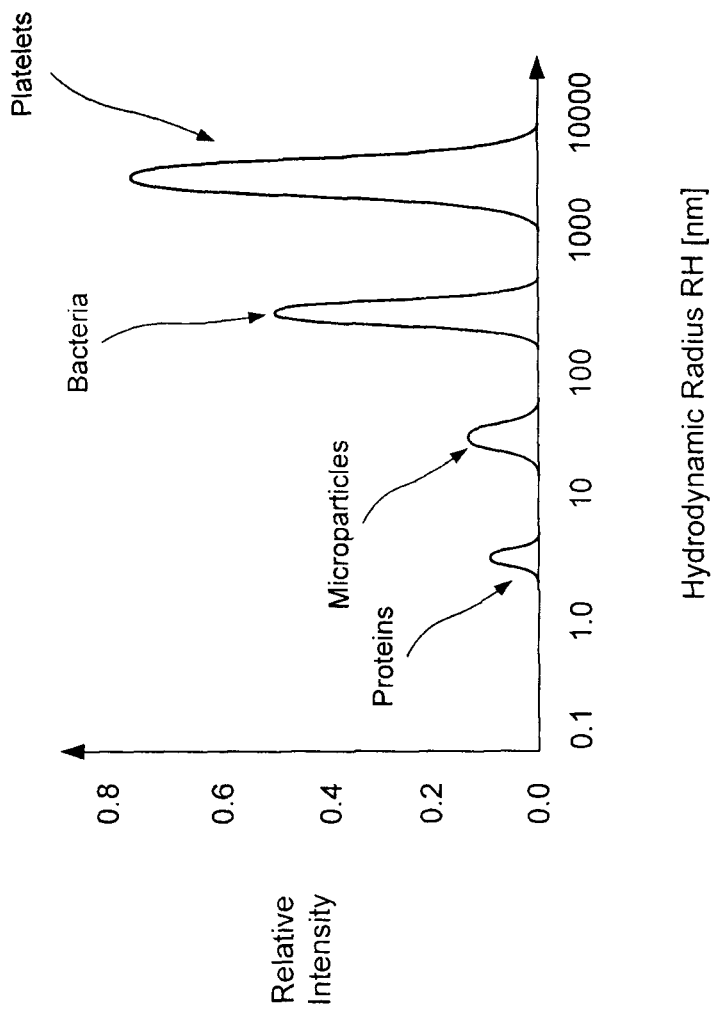
FIG. 2 is a graph plotting a representative distribution of hydrodynamic radii as a function of light intensity obtained from a DLS "speckle pattern" of platelets, bacteria, microparticles (MPs) and proteins as could be obtained using the DLS system shown in FIG. 1.

The computer 28 (running the software correlator) generates a correlation function and then generates a size distribution plot, such as the one shown in FIG. 2, for graphical presentation to a researcher or other end-user. Alternatively, size distribution data can be presented in tabular form or in any other intelligible manner.

As depicted in FIG. 2, the size distribution plot shows a representative distribution of hydrodynamic radii for platelets, bacteria, microparticles and proteins although it should be expressly understood that the hydrodynamic radii, relative intensities and particle distributions shown are not meant to represent actual values or distributions. The hydrodynamic radii are calculated from the DLS "speckle pattern", as is known in the art. The size distribution plot readily enables researchers, technicians, clinicians or other end-users to detect the presence of bacteria in a sample of platelet concentrate. This applies to both measurement types of dynamic scattering, i.e. not only forward scattering through a small capillary or similar device but also back scattering from a platelet bag with an optical access window or a flat (optically translucent) container.

In one embodiment, the computer 28 generates (and displays) data 32 on bacterial contamination. The computer 28 can generate data on the quantity of bacteria and whether the quantity of bacteria exceeds a predetermined threshold. The computer can also attempt to identify the bacterial species by comparing its mean particle size with previously obtained empirical data. The computer can also be used to trigger an alarm if the level of bacteria exceeds the threshold.

The DLS system can also determine platelet quality based on three independent factors, namely (i) the mean hydrodynamic radius of the platelets, (ii) the relative number of microparticles (MPs) and (iii) the platelet response to temperature cycling. A computational matrix quantifies platelet quality as a function of mean hydrodynamic radius (RH), MP concentration, and temperature response (TR). The three measures are combined to one number called the DLS score, which enables automated platelet scoring because the system can simultaneously measure and input into the computational matrix all three of these independent parameters, thus providing very high analytic sensitivity for platelet quality determinations. This methodology is described in detail in applicant's U.S. Ser. No. 10/925,779 (Maurer) filed Aug. 24, 2004 and entitled METHOD FOR DETERMINATION OF PLATELETS QUALITY, which is hereby incorporated by reference. It should be expressly understood that this system can be used not only for DLS analysis of platelets in suspension, but also for analyzing whole blood or other colloids or colloidal dispersions. Bacterial toxins have a negative effect on platelet quality and will therefore cause a low DLS score.

Figure 3:
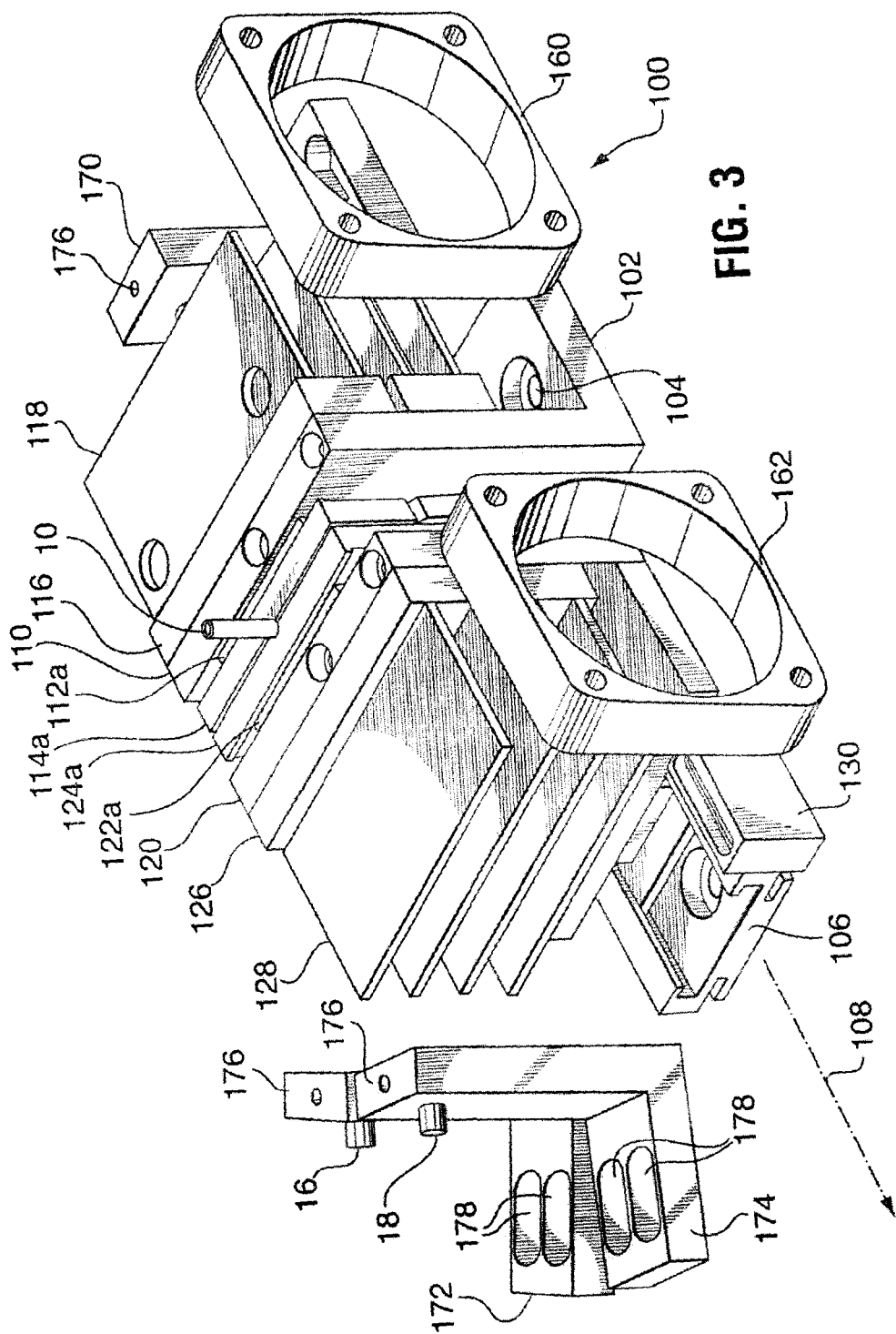
FIG. 3 is an isometric perspective view of a sample holder for use in the system shown in FIG. 1, wherein sample holder is in a closed, gripping position.

FIG. 3 illustrates the sample holder 100 in accordance with a preferred embodiment of the present invention. The sample holder 100 (also referred to herein as a sample-holding device) has a stationary base 102 which has a substantially flat underside for sitting upon a flat surface such as a workbench, lab counter, table, base plate or the like. The base preferably includes one or more bores through which a fastener could be inserted to securely mount the base to a base plate, table, workbench, lab countertop or the like. It is preferable that the base 102 of the sample holder 100 be securely attached to an immovable structure to improve measurement precision and to avoid having to frequently recalibrate the DLS system. In the embodiments depicted in FIG. 1B and FIG. 1C, the backing member of the sample-holding device is preferably mounted to a flat surface such as, for example, a workbench, lab counter, table, base plate or the like that has an opening for optical fiber access.

The base 102 preferably includes a rectilinear rail 106 defining a displacement axis 108. For manufacturability, the rail 106 and base 102 are preferably machined or cast as separate components and secured to each other by threaded fasteners (to thus define a "two-part base"). Alternatively, it would also be possible for the rail 106 to be made integral with the base 102 (to define a unitary base). In any event, the base 102 has a connected rail portion 106 that together supports the rest of the sample holder.

The sample holder 100 further includes an upright backing member 110 (i.e. a fixed, upright wall) and a movable clamping member 120 (i.e. a movable upright member) that can move relative to the backing member (or wall) 110 between an open, retracted position, in which the clamping member 120 no longer contacts the container 10 (i.e. the movable upright member and the wall are separated by a distance greater than an outer diameter of the container 10) and a closed, holding (or "gripping") position, in which the clamping member (movable upright member) 120 presses against the container 10 to lightly and gently clamp or hold the container 10 between the clamping member 120 (movable member) and the backing member (wall) 110 whereby the container 10 is immobilized for optical analysis of the fluid sample in the container 10. While the illustrated embodiments of the sample holder were designed for optical analysis such as DLS or QELS, the sample holder (or variants thereof) can also be used for static light scattering or as part of a spectrofluorometer. Preferably, the backing member 110 is integral with the base 102. Similarly, in the preferred embodiment, the movable member 120 is integrally formed with a horizontally disposed sliding plate 120a that engages and slides over the rail 106.

In a preferred embodiment, the movable upright member 120 slides relative to the stationary wall member 110, guided by the rail 106 so that the movable member 120 is constrained to translate along the displacement axis 108. The displacement axis 108, as shown in FIG. 3, is substantially perpendicular to the backing and clamping members 110, 120. While sliding, or translational, motion is preferred, the movable upright member 120 could also be made to rotate relative to the wall 110 using pivots or hinges. The movable upright member 120 could also be made to slide along a vertical axis or a different horizontal axis, i.e. an axis orthogonal to the illustrated displacement axis 108. Alternatively, the sample holder 100, could use compound motion (both rotation and translation) to open and close the clamping member relative to the fixed, upright wall member.

Figure 5A:
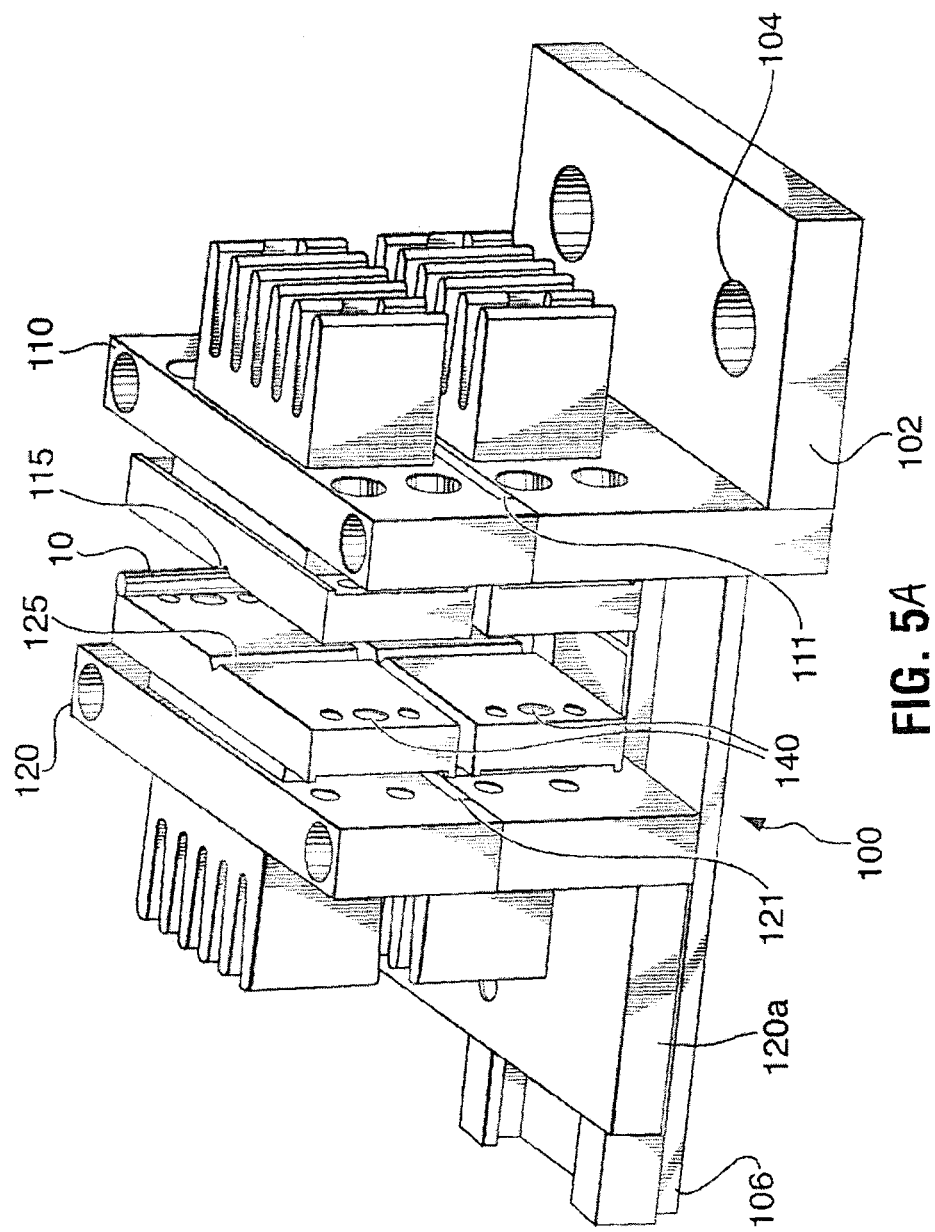
FIG. 5A is an isometric perspective view of another version of the sample holder shown in FIG. 3, shown this time in an open, retracted position.

The sample holder can further include a plurality of magnets 140 for biasing the movable member 120 toward the wall 110. Preferably, four pairs of cylindrical, oppositely poled magnets 140 are embedded in bores in the movable member (as shown in FIG. 5A) and in the wall which thus provide a uniform magnetic force of attraction in substantial alignment with the displacement axis 108. The magnets 140 are designed to generate a magnetic force of attraction that, when the movable upright member is in the gripping position, is large enough to securely hold the container between the movable upright member and the wall but small enough to preclude deformation of the container and also small enough to enable a user to easily manually separate the movable upright member and the wall by manually forcing the movable upright member to the retracted position.

As shown in FIG. 3, the sample holder 100 can include a slider stopper 130, which can be secured to the rail 106 (or to the base plate) using one or more threaded fasteners (not shown). The slider stopper 130 limits the sliding displacement of the movable member 120 away from the wall 110. When the movable member reaches the slider stopper 130, the movable member is in the open, retracted position (which is shown in FIG. 5A).

Figure 4:
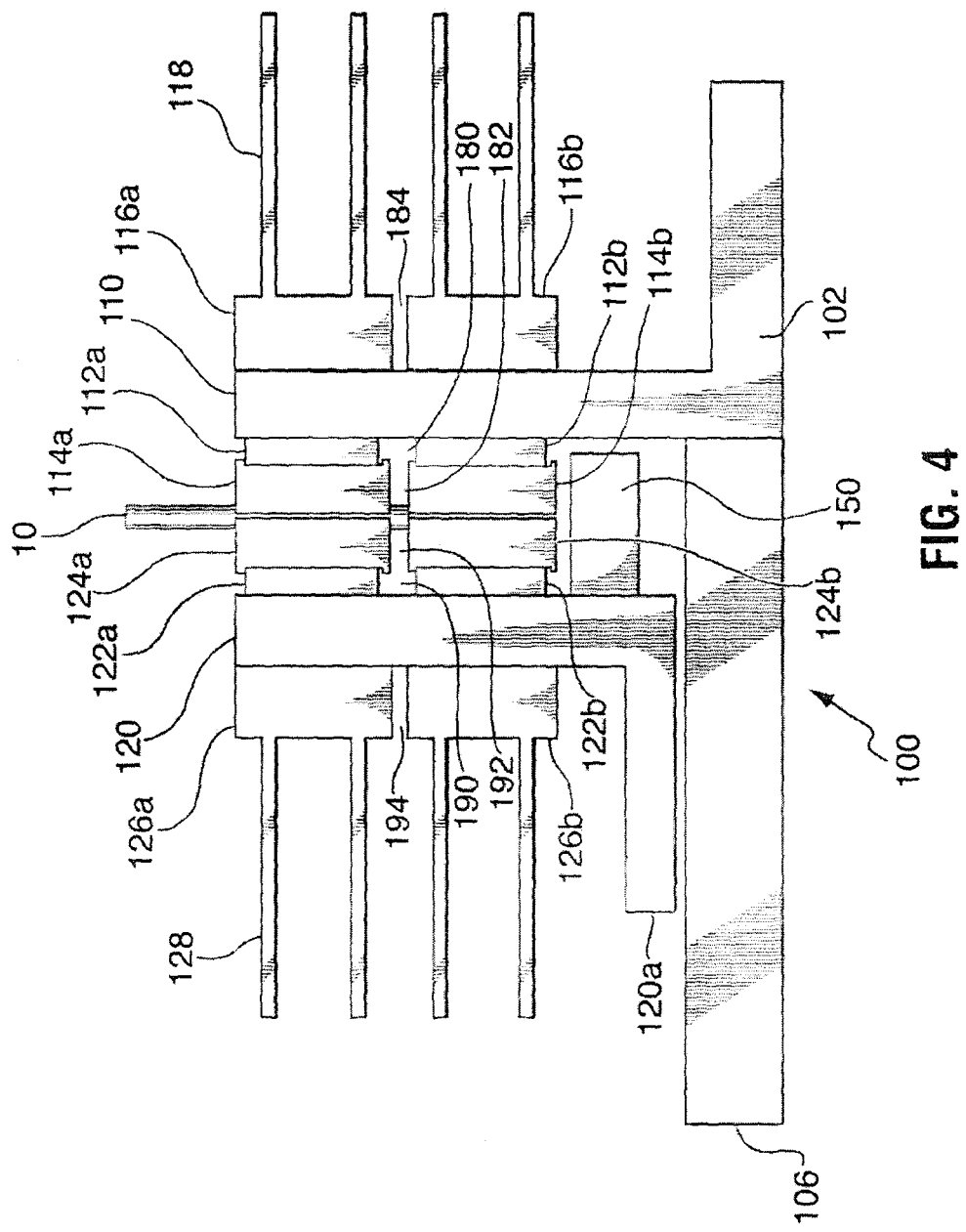
FIG. 4 is a side view of the sample holder shown in FIG. 3, but illustrated without the fans and fiber-holding brackets, also shown in the closed position.

FIG. 4 is a side elevational view of the sample holder 100 shown in FIG. 3, but depicted without the fans and fiber-holding brackets. As shown in FIGS. 3 and 4, the sample holder 100 has a first pair of vertically spaced-apart heating/cooling elements 112a, 112b connected to an inwardly facing surface of the backing member 110, the first pair of heating/cooling elements being capable of transferring heat to or from the fluid sample in the container 10, which can be plastic tubing. For the purposes of this specification, "vertically spaced-apart" means that there is an upper component and a lower component separated by a gap. Also for the purposes of this specification, "inwardly facing" means facing toward the sample container and thus "outwardly facing" means facing away from the sample container.

The sample holder 100 also includes a first pair of vertically spaced-apart heat-conductive plates 114a, 114b connected to inwardly facing surfaces of the first pair of heating/cooling elements 112a, 112b for conducting heat to or from the container to thus either cool or heat the fluid sample.

The sample holder 100 further includes a second pair of vertically spaced-apart heating/cooling elements 122a, 122b connected to an inwardly facing surface of the movable clamping member 120, the second pair of heating/cooling elements being capable of transferring heat to or from the fluid sample in the container 10. The sample holder 100 further includes a second pair of heat-conductive plates 124a, 124b connected to inwardly facing surfaces of the second pair of heating/cooling elements 122a, 122b for conducting heat to or from the container 10 to thus cool or heat the fluid sample. The heating/cooling elements can be attached to the movable member using studs and bores, threaded fasteners or other known mechanical fasteners. Likewise, the heat-conductive plates can be attached to the heating/cooling elements using studs and bores, threaded fasteners or other known mechanical fasteners.

To recap, therefore, there are four heating/cooling elements 112a, 112b, 122a, 122b and four attached plates 114a, 114b, 124a, 124b in the preferred embodiment, as shown in FIG. 4. The vertically spaced-apart pairs of heating/cooling elements define first gaps 180, 190. The vertically spaced-apart pairs of plates likewise define second gaps 182, 192. The first gaps 180, 190 are aligned with the second gaps 182, 192, as shown in FIG. 4. Furthermore, the wall 110 and the movable member 120 have substantially horizontal slots 111, 121 (optical access slots or slits) that also align with the gaps 180, 190, 182, 192 on either side of the device to minimally obstruct optical access to the fluid sample in the translucent container 10. Furthermore, as shown in FIG. 4, the sample holder 100 has upper and lower heat sinks 116a, 116b attached to the outwardly facing surface of the wall 110 as well as upper and lower heat sinks 126a, 126b attached to the outwardly facing surface of the movable member 120. The heat sinks can be attached to the wall and movable member using studs in bores, threaded fasteners or other known mechanical fasteners. As shown in FIG. 4, the upper heat sinks 116a, 126a are disposed above the slots 111, 121 in the wall 110 and movable member 120 while the lower heat sinks 116b, 126b are disposed below the slots 111, 121. This heat sink design also minimally obstructs optical access to the fluid sample in the container 10. These upper and lower heat sinks define on each side of the device third gaps 184, 194 which are also aligned with the first gaps 180, 190, the second gaps 182, 192 and the slots 111, 121.

Preferably, the heating/cooling elements 112, 122 are Peltier-type thermoelectric devices with microthermocouples for temperature sensing and feedback control. Peltier heater/cooler devices are also known in the art as thermoelectric modules. These Peltier-type thermoelectric modules are small solid-state devices that function as heat pumps. Usually, a Peltier device has a "sandwich" structure formed by two ceramic plates with an array of small Bismuth Telluride cubes ("couples") in between. When a DC current is applied to the device, heat is transferred from one side to the other, where it must be removed with a heat sink. By placing the "cold" side facing the heat-conductive plate, the sample can thus be cooled. If the current is reversed, the Peltier device heat is transferred to the inner side and this heats the sample. These Peltier thermoelectric modules enable the sample holder 100 to rapidly control the temperature of the sample, e.g. for bringing the sample to the desired temperature and for performing temperature cycling. In the case where the whole bag setup is used, such as in FIG. 1C, a stable temperature of 22° C. would be maintained but no temperature cycling would be performed. A modified DLS score would be calculated that does not contain the temperature response information.

As noted above and shown in FIGS. 3 and 4, the sample holder 100 preferably includes heat sinks 116, 126 connected to outwardly facing surfaces of the wall and movable member, respectively. These heat sinks 116, 126 can include fins 118, 128, respectively. The fins can be horizontal (as shown in the embodiment of FIGS. 3 and 4) or vertical (as shown in the embodiment of FIG. 5A). In any event, the finned heat sinks cooperate with the Peltier devices to cool the fluid sample by drawing heat away from the hot side of the Peltier devices.

In a preferred embodiment, the sample holder 100 includes fans 160, 162 for further improving the cooling efficiency of the Peltier devices by augmenting convective heat transfer of the finned heat sinks. It should be noted that the fans could be part of the sample holder 100 or they could be separate components (but nonetheless part of the DLS system). It should be noted that it is preferable to have the fans to improve cooling efficiency but they are not essential.

As further shown in FIG. 3, the sample holder can include a plurality of fiber-holding brackets 170, 172, 174 for holding the optical fibers at the same height as the slots to ensure that the incident light hits the sample and that the scattered light from the sample can be captured by the light-collecting fibers 16, 18. The optical fibers have either a focusing or collimating lens to narrow the laser beam so that illuminated sample volume is small, i.e. ideally one or only a few coherence volumes. This requires the ends of the optical fibers to be one focal length away from the center of the sample. The fiber holders 170, 172, 174 are thus mounted relative to the sample in order to provide distances to the sample that are each equal to the focal length. In a preferred embodiment, a first L-shaped bracket 170 holds the optical fiber 6 connected to the laser diode 2 or other optical source (referring back to FIG. 1) whereas second and third L-shaped brackets 172, 174 hold the light-collecting fibers 16, 18, respectively. Other brackets would, of course, be provided if additional light-collecting fibers are to be used to capture scattered light. As shown in FIG. 3, each of the L-shaped brackets includes a top threaded bore 176 for receiving a set screw (not shown) which can be used to fix the optical fiber in the bracket to ensure alignment with the plane of the slots. As shown in FIG. 3, each of the L-shaped brackets also includes a footing with an oblong slot through which a fastener can be inserted to secure the brackets to a bench, table, counter, base plate or other such surface.

In this embodiment, only a single light source is used and scattered light is collected by a plurality of light collectors. For example, the light collectors can be spaced at 15-degree intervals from each other. In one configuration, one light collector could be set up at a 45-degree angle from the incident light with a second collector at a 60-degree angle (again with respect to the incident light). Alternatively, the light collectors (or additional collectors) could be set up at 30 and 90 degrees. However, it should be appreciated that multiple light sources could be used as well and the number of light collectors and their respective angles or positions could also be varied. The sample holder 100 therefore enables a user to simultaneously obtain measurements at one or more scattering angles.

As further shown in FIG. 4, while the sample holder 100 could include an elevated footrest 150 securely connected to a bottom portion of the movable member 120, this footrest is not required when using a tubing, particular a tubing still attached to its bag. Also, if a horizontal setup is used, the footrest would not be needed as the sample container would rest on the backing of the sample holder.

FIG. 5A illustrates the sample holder 100 in accordance with another embodiment of the present invention, shown in the open, retracted position. While a vertical (upright) setup is preferred, the setup could be horizontal as well. FIG. 5A shows that the backing member 110 and the clamping member 120 include, respectively, first and second grooved plates 114, 124 facing each other in a generally parallel arrangement and having opposed, substantially vertical grooves 115, 125 for holding the fluid container (or tube) 10 in a substantially vertical orientation. The plates 114, 124 could also have knurling or other surface finishing that enhances adherence to glass or plastic so as to promote gripping of the glass or plastic capillaries or cuvettes. As shown, the grooves 115, 125 could have V-shaped profiles to grip a variety of differently sized, elongated tubular or square containers, such as capillaries or cuvettes. V-shaped grooves are generally preferred because they promote excellent heat transfer to or from a variety of differently sized and differently shaped containers. Alternatively, the grooves could have semicircular or rectangular profiles to grip capillaries or cuvettes having substantially round or substantially square cross-sections. To optimize heat transfer efficiency, the grooves should provide a substantially exact fit with the capillary or cuvette, although an exact fit is of course not necessary. In other words, semicircular or rectangular grooves can also be used to hold variably sized containers. Preferably, the sample container 10 is a disposable, glass or plastic capillary with round or square geometry and having a diameter of about 2 mm and a volume of about 30 microliters, although the sample holder 100 is designed to accommodate a range of sizes and therefore these dimensions should not be considered as limiting the scope of the invention. This sample holder can be used to hold a small plastic tubing, or tube, that is appended to a platelet storage bag, as will be elaborated below.

Figure 5B:
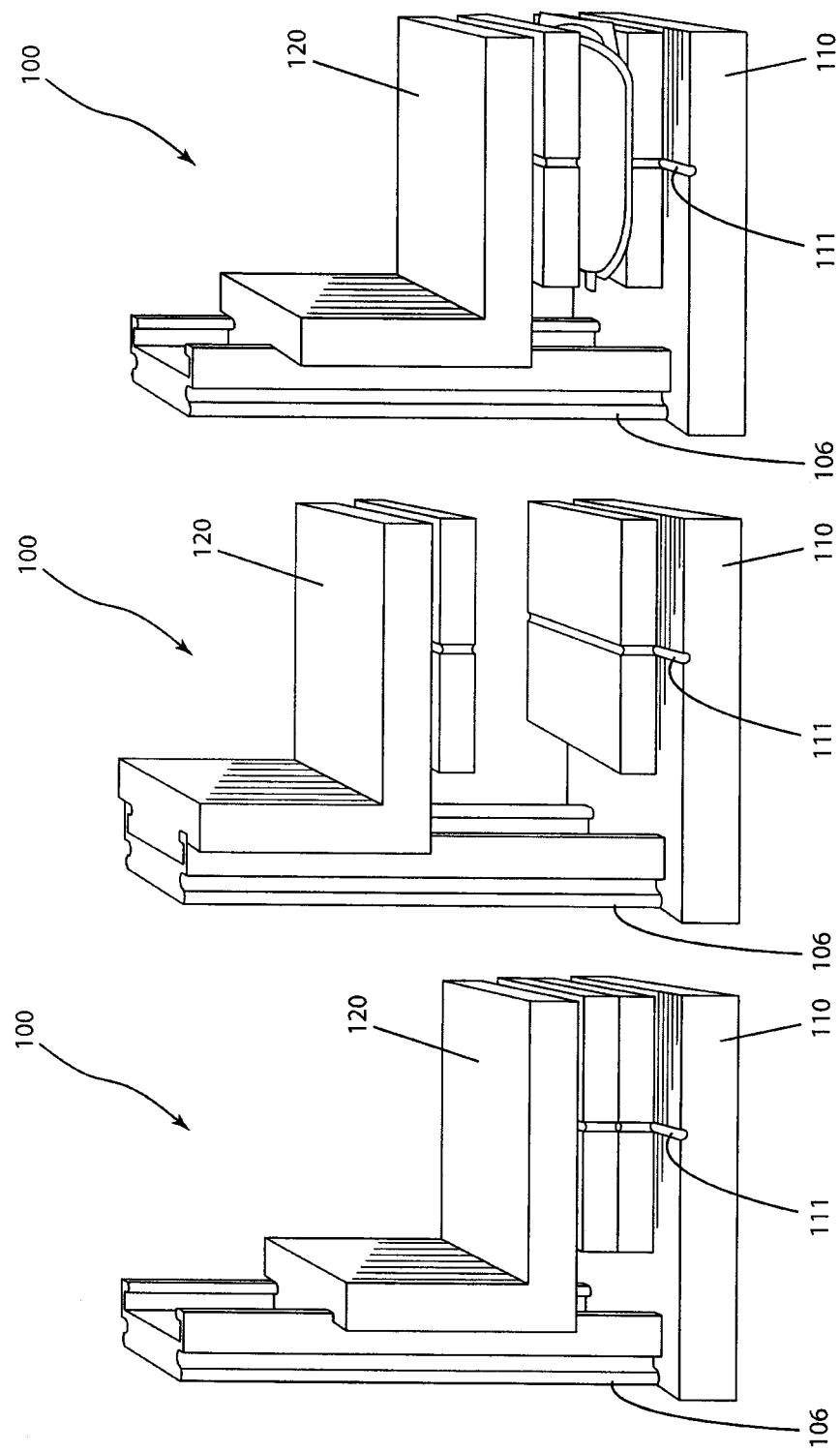
FIG. 5B is a modified sample holder that receives and accurately positions a whole platelet storage bag that has been modified to include an optical access window so that the incident and scattered light fibers can deliver and collect light through the optical access window.

FIG. 5B illustrates a modified sample holder 100 in accordance with another embodiment of the present invention, shown, respectively, from left to right, in a closed (inactive) position, an open (but empty) position and an operating position (holding a modified platelet bag). This horizontal setup allows placement and retention of a whole platelet bag such that the optically translucent window faces the light-access slit. This sample holder 100 can be utilized in a dynamic light scattering instrument such as the one shown by way of example in FIG. 1B.

As shown in FIG. 1C, a system for detecting bacterial contamination of a platelet concentrate includes a platelet storage bag containing a platelet concentrate, the bag having an optically translucent window in a wall of the bag through which light can pass. The system of FIG. 1C also includes a sample holder (such as the one shown in FIG. 5B) for holding the bag between a stationary clamping member 110 and a movable clamping member 120 such that the optically translucent window aligns with an optical access slot in the stationary clamping member. Optionally, the movable clamping member of the sample holder is slidable along a substantially vertically disposed rail 106.

The system of FIG. 1C also includes a light source for directing a beam of light through the optical access slot 111 of the stationary clamping member 110 and through the optically translucent window 250 of the platelet storage bag 200, a light collector for collecting backscattered light exiting through the optically translucent window of the bag and through the optical access slot of the stationary clamping member, and a correlating means for correlating collected backscattered light to particle size to determine whether the platelet concentrate in the bag is contaminated.

Each of these systems therefore can perform a duality of functions: (i) bacteria detection and contamination alerting and (ii) platelet quality assessment, i.e. whether the platelets are "fresh" (i.e. of good quality) or "stale" (i.e. no longer useful for transfusion). Both of these tests/assessments provide crucial information about the platelet concentrate prior to transfusion, thus minimizing the risks that poor quality and/or contaminated platelets are transfused into a patient. Furthermore, because the system is easy to use, highly sensitive and provides quick results, it becomes a natural candidate as a point-of-care (pre-transfusion) test.

Figure 6A:
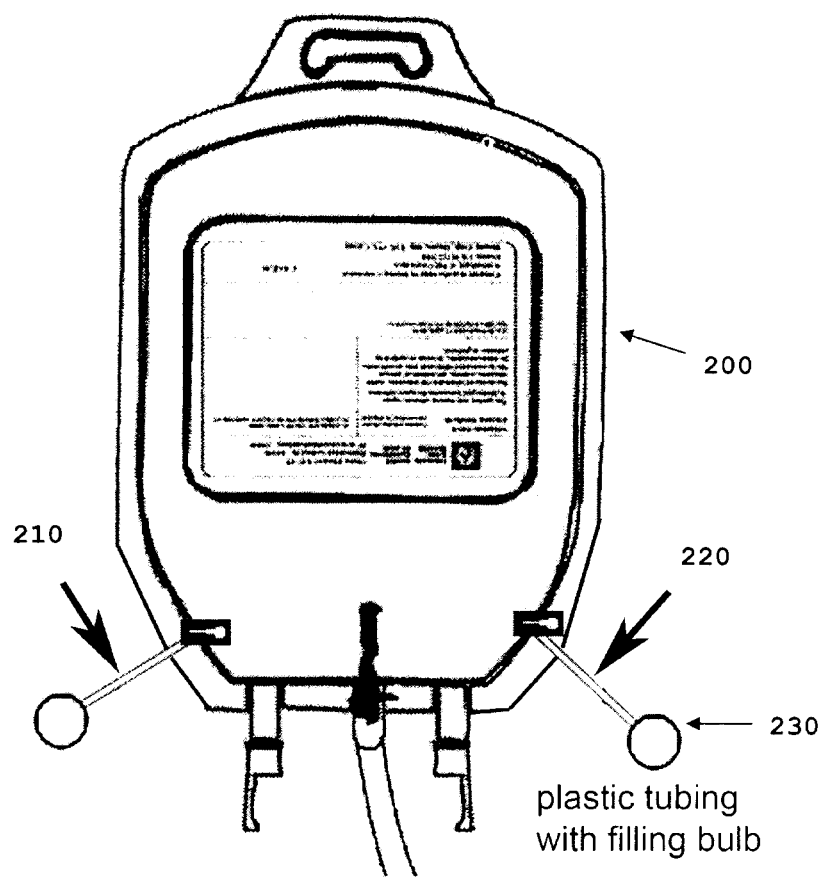
FIG. 6A is a front view of a platelet storage bag having two appended tubes for insertion into one of the capillary-holding sample holders such as the one shown in FIG. 5A in order to perform DLS bacteria detection.

FIG. 6A depicts a platelet storage bag 200 in accordance with another embodiment of the present invention. The platelet storage bag has at least one tube 210 appended in selective fluid communication with the bag, the tube 210 being sufficiently rigid to resist deformation when held in a substantially vertical orientation between clamping faces of the sample holder (i.e. of the bacteria detection system). A rigid, or semi-rigid, plastic tubing can be held by the sample holder described above. Each tubing (or tube) enables a user to draw a sample from the concentrate storage bag for DLS testing. In other words, after thorough, gentle mixing of the platelet concentrate, the appended sample tubing is loaded by drawing the sample into the tubing. For testing, the tubing is either detached from the bag or left attached to the bag. For the whole bag setup (such as the setup shown in FIG. 10) an optically transparent window enables access for the incident light and collection of the back scattered light. The window could be a heat-pressed spot of the platelet bag with an area of, for example, 1 cm².

Preferably, as depicted in FIG. 6A, the bag has a plurality of tubes 210, 220 to enable multiple samples to be drawn over time. As will be appreciated, although the bag shown in this figure has only 2 tubes, the bag can have three or more "appendices" (tubes) to enable repeated/multiple sampling of representative aliquots.

As shown in FIG. 6A, the bag can include a filling bulb 230 at the end of each tube 210, 220 to facilitate suction-loading (drawing) of a sample into the tubing. However, depending on the properties of the tubing, this filling bulb might not be necessary (i.e. the tubing itself could be squeezed for filling). Alternatively, the filling bulb could be detached after filling by the use of a sealer. The tubing would stay attached to the bag thereby being barcode-labeled and identifiable. The plastic tubing of the appendix can then be inserted into the sample holder. The tubing functions as a measurement container and is aligned, centered and temperature-controlled, as desired. If the unit is to remain in the platelet shaker but extended measurements on the sample contained in the appendix are required for a long period of time, then the tubing 210, 220 should be detached. This could be the case when low levels of bacterial contamination need to be quickly verified. By incubating the tubing/sample container at 37° C. multiplication of bacteria are accelerated and leads to a stronger signal when measured again after incubation as described below.

Use of this novel platelet storage bag enables non-invasive sampling of platelet concentrates, i.e. no needle sampling is required and therefore there is no breach of sterility. The same tubing also functions as the measurement capillary for dynamic light scattering in a system such as the one shown in FIG. 1. The technique requires only small volumes of platelet concentrate (e.g. 30-100 microliters are typically required). Such a small volume is required because this novel DLS technique is highly sensitive, i.e. substantially more sensitive than prior-art techniques. For example, the level of bacterial contamination detectable by this new dynamic light scattering technique is believed to be far below the detection limit of the BacT/ALERT®.

Figure 6B:
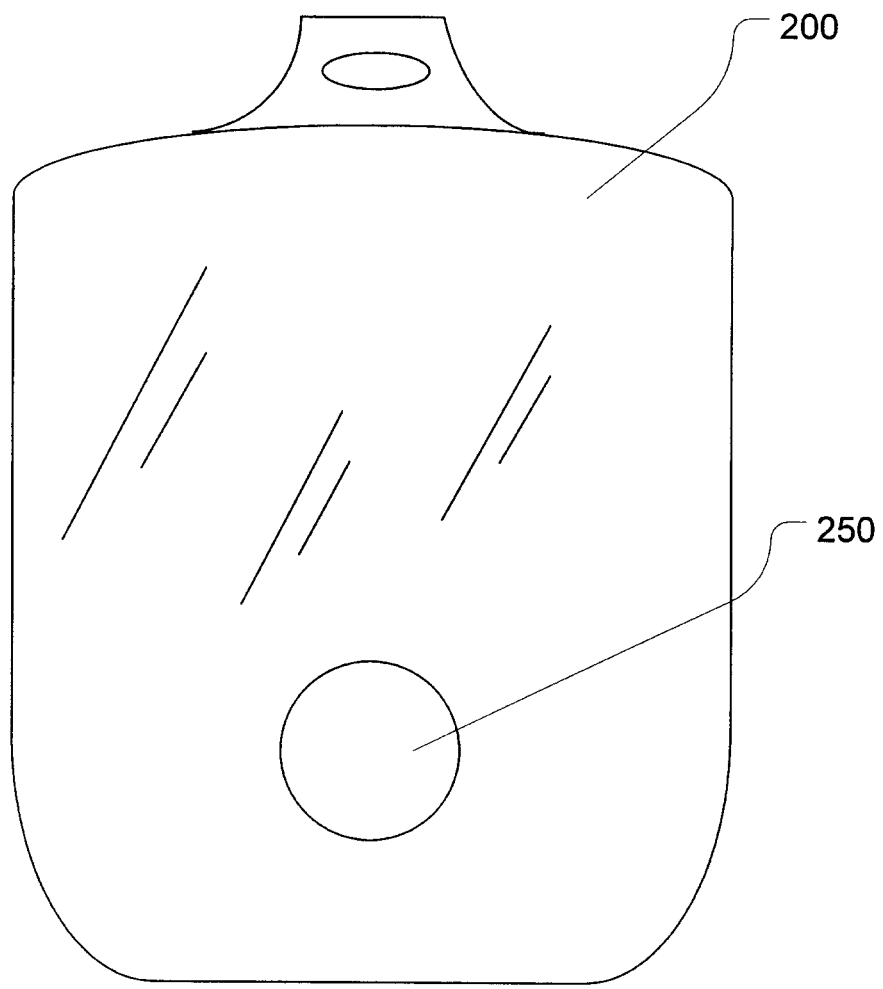
FIG. 6B is a front view of a platelet storage bag having an optical access window through which the platelet sample can be illuminated and through which scattered light can be collected at a large scattering angle.

FIG. 6B is a front view of another novel platelet storage bag 200 having an optical access window through which the platelet sample can be illuminated and through which scattered light can be collected at a large scattering angle. The optical access window is preferably an optically translucent window 250 formed in the wall of the bag. It will be appreciated that this bag can have more than one optical access window. The modified sample holder shown in FIG. 5B preferably includes positioning pins or positioning guides (not shown) for locating the bag 200 such that its optical access window 250 aligns with the optical access slot (or "slit") 111 formed in the stationary clamping member 110 of the sample holder 100.

In yet another embodiment, the platelet storage bag could be designed to have both the detachably appended tubes and at least one optical access window so that the technician, clinician or other end-user could choose to use one type of sample holder or another depending on availability or other factors.

Method of Detecting Bacteria Using DLS

The method for detecting bacteria in a sample, such as a platelet concentrate, includes steps of placing the sample in a dynamic light scattering (DLS) instrument, collecting DLS measurements from the sample, and determining whether bacteria are present in the sample based on the DLS measurements from the sample.

In one embodiment, the step of determining whether bacteria are present in the sample involves steps of determining a relative intensity of scattered light relative to incident light for a range of particle sizes to thus create a size distribution having discrete peaks corresponding to different types of particles. The platelets, microparticles, proteins and bacteria are then discriminated based on expected locations of the discrete peaks in the size distribution. The quantity of bacteria in the sample can then be estimated based on the relative intensity of the scattered light found at a particle size that is known to correspond to the particle size of the bacteria.

Before placing the sample into the DLS instrument, the sample is preferably loaded into a tubing (i.e. a thin-gauge tube that functions as a capillary) appended to a bag containing a volume of platelet concentrate. The tubing is in selective fluid communication with the bag so that a user can draw ("suction-load") the sample into the tubing. The tubing can either be detached from the bag (after loading the sample of platelet concentrate into the tubing) to facilitate insertion of the tubing into the DLS instrument or, alternatively, the tubing can be inserted into the DLS instrument with the tubing still attached to the bag. If the bag has multiple tubes, then multiple tests can be performed at various points in time by drawing successive samples into each of the multiple tubes.

In one embodiment, a platelet storage bag with an optical access window is placed into the light scattering device (or sample holder) at any time bacterial testing is required.

In one embodiment, the step of determining whether bacteria are present in the sample entails identifying a specific species of bacteria in the sample by correlating a mean particle size to a specific species of bacteria based on previously determined empirical data for the particular species of bacteria. In other words, empirical data for mean particle size is obtained using the DLS instrument for various species of bacteria by using known techniques such as phase contrast microscopy to identify the different species of bacteria. Once this empirical data is obtained, then it becomes fairly straightforward to predict the species of bacteria from the DLS results, i.e. the mean particle size (as determined by the intensity peaks). However, it should be borne in mind that, for clinical utility, identifying the particular species is usually of far lesser importance than simply determining that the sample is, in fact, contaminated.

Indeed, discriminating the bacteria can be accomplished by identifying the platelets, microparticles, proteins and bacteria by comparing mean particle sizes to expected particle size ranges for platelets, microparticles, proteins and bacteria, respectively, based on previously obtained empirical data. In other words, expected size ranges can be established based on empirical data so that platelets, microparticles, and proteins can be identified, thus enabling rapid and easy discrimination of bacteria (which manifest themselves as intensity peaks in other regions of the size distribution).

Even if appreciable numbers of bacteria are not present or the bacteria are not viable anymore the released toxins activate platelets and reduce the DLS score. This is a significant advantage compared to culture methods that require live bacteria to obtain a positive result. Bacterial detection based on the negative effect on platelets is particularly important for Gram-negative bacteria, which are generally not serotolerant but produce very harmful toxins.

Bacterial contamination is further indicated by the total scattering intensity. After calibration of the scattering device with known concentration of standard latex beads, a significantly higher total scattering intensity (50% above the upper calibration limit) indicates a high number of additional scattering particles. Because a platelet concentrate is a closed system and platelets cannot multiply an increase in scattering particles can only originate from multiplying contaminants. On the other hand, a significantly lower total scattering intensity (50% below the lower calibration limit) indicates the loss of scattering particles as a consequence of platelet aggregation. Bacterial toxins can initiate platelet aggregation and bacteria can directly crosslink platelets.

The presence of bacteria or their platelet-activating and aggregating effects significantly reduce the DLS score. Platelet concentrates which do not reach a predetermined acceptable DLS score are not deemed appropriate for transfusion. Platelet concentrates with abnormally high or low total scattering intensities automatically receive a low DLS score.

If the DLS instrument is capable of heating and/or cooling the sample, then the method can be further refined to improve the sensitivity of the technique (which thus enables the refined method to further discriminate the bacteria from the platelets). This refined method therefore identifies bacteria not only by their size but discriminates the bacterial dynamic light scattering signal from the other dynamic light scattering contributions in two ways: although bacteria multiply during incubation at 37° C., the size of the bacteria remains approximately the same. Therefore, the intensity of the dynamic light scattering signal due to the bacteria increases over time. This amplification of the number of bacteria through incubation at 37° C. increases the sensitivity of the method when the number of bacteria in the solution is still low. Secondly, the size of bacteria does not change with temperature cycling. In contrast, platelets undergo a temperature-dependent shape change when cooled from 37° C. to 20° C., which is seen as an increase in platelet size.

Since both bacterial amplification and lack of temperature response require accurate temperature control, this method is best implemented using the sample holder described above (such as the ones shown in FIGS. 1A and 1B).

Figure 7A:
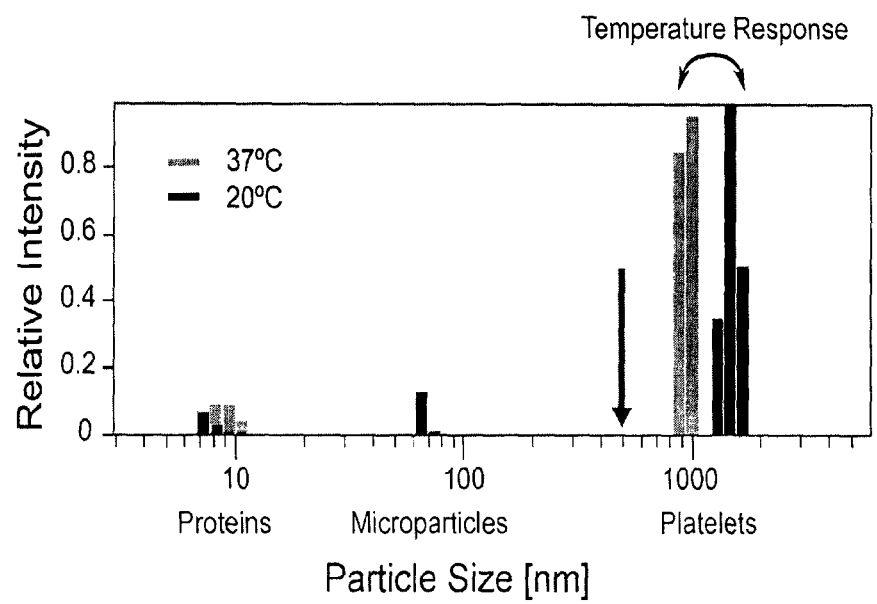
FIG. 7A is a size distribution showing peaks corresponding to distinct populations of platelets, microparticles and proteins.
Figure 7B:
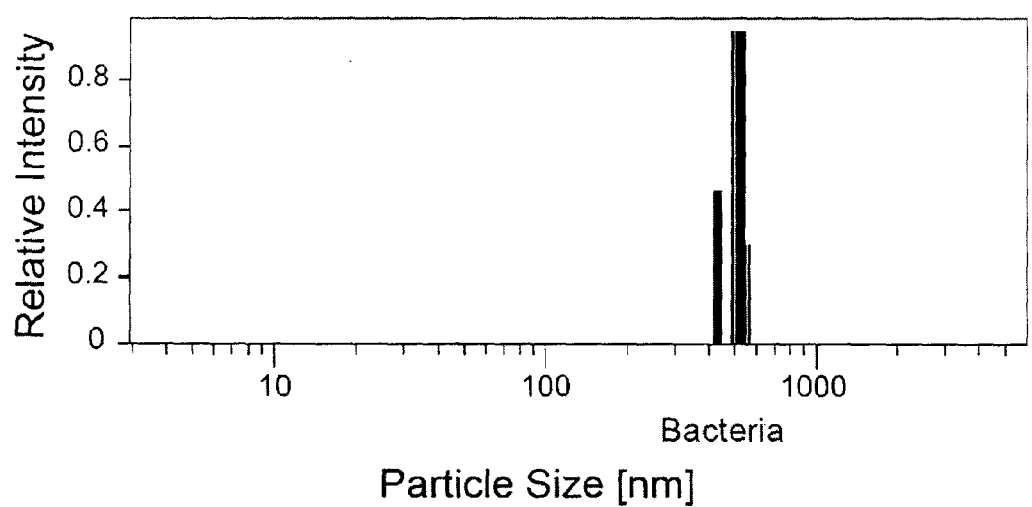
FIG. 7B is a size distribution showing a peak corresponding to a particular species of bacteria.

FIG. 7A shows a size distribution for fresh platelet-rich plasma while FIG. 7B shows a distribution for bacteria, both acquired using dynamic light scattering (DLS). In the size distribution presented in FIG. 7A, the platelets are characterized by size and temperature response. The size distributions of fresh platelets at 37° C. (grey) and temperature-activated platelets at 20° C. (black) are shown. All particles in solution contribute to the signal, which are proteins, microparticles budding off as a response to temperature activation in fresh platelet samples, and platelets. Platelet shape change is detected as increase in hydrodynamic radius (particle size) because the highly irregular form of "spiny spheres" increases the friction and slows platelet movement. The arrow indicates where the signal for bacteria would be expected. The size distribution presented in FIG. 7B shows dynamic light scattering results of *Staphylococcus epidermidis* in buffer.

Figure 8A:
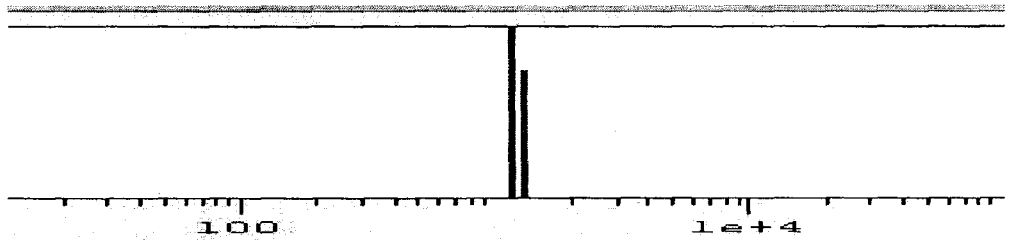
FIG. 8A is a DLS-derived size distribution of a platelet concentrate sample (apheresis unit) on day 1.
Figure 8B:
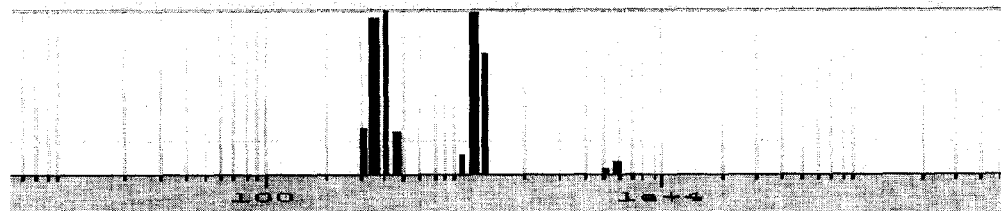
FIG. 8B is a DLS-derived size distribution of a platelet concentrate sample on day 8.
Figure 8C:
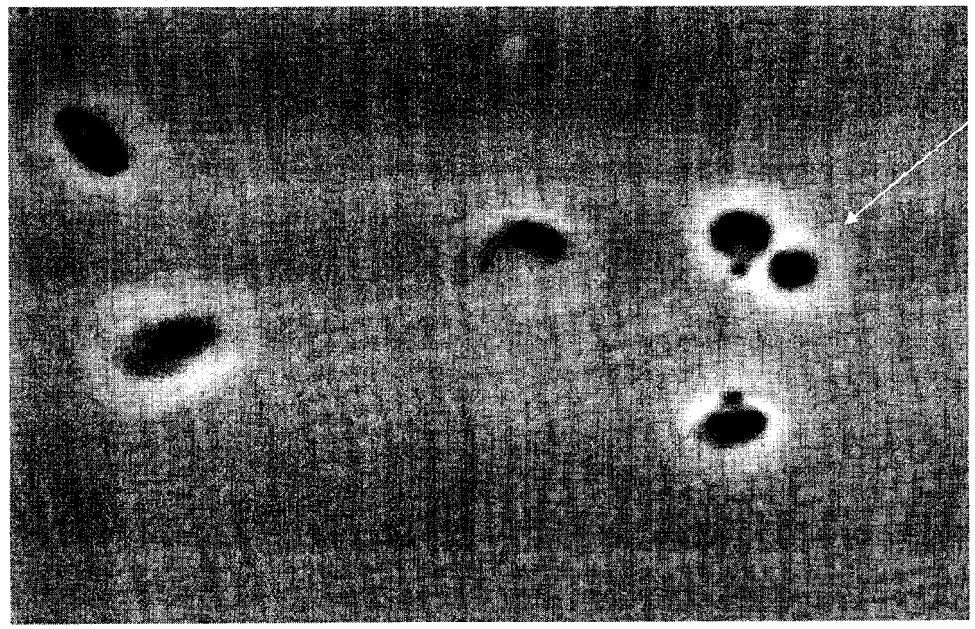
FIG. 8C is a phase contrast microscopy image taken during morphology scoring on day 6.
Figure 8D:
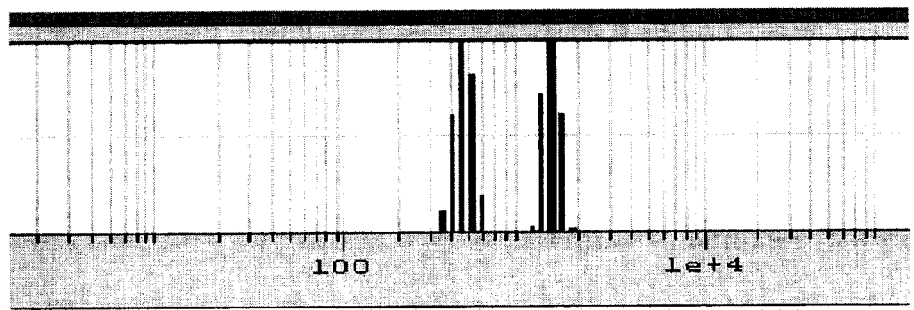
FIG. 8D is a DLS-derived size distribution of a platelet concentrate sample on day 12.
Figure 8E:
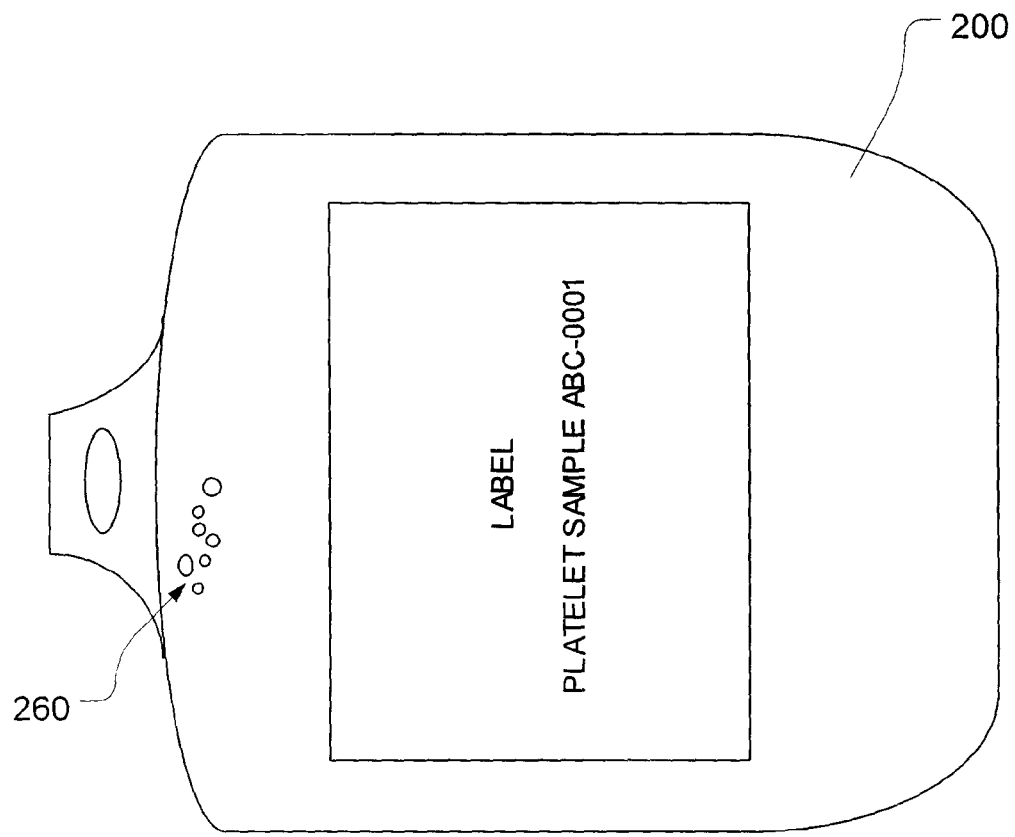
FIG. 8E is a schematic depiction based on a photograph of a platelet storage bag having zones where deposition of bacterial aggregates are visible.

FIGS. 8A, 8B and 8D present, respectively, DLS-derived size distributions of a platelet concentrate sample (apheresis unit) on day 1 following preparation and again on days 8 and 12. The size distribution analysis presented in FIG. 8A shows platelets on day 1 at 37° C. with a mean radius for the platelet population of 1220±90 nm. The size distribution analysis presented in FIG. 8B is for day 8, on which platelets at 20° C. had a mean radius of 1170±100 nm and bacteria appeared after 12 minutes of measurement time with a mean radius of 360±90 nm. The DLS score dropped from 23 (day 1) to 8. As shown in FIG. 8C, the presence of bacteria was also indicated in phase contrast microscopy images taken during morphology scoring on day 6. As shown in the size analysis of FIG. 8D, on day 12 of storage, bacterial contamination was already detected after 5 minutes of measurement time. The mean radius of platelets was 1440±160 nm and of bacteria was 470±60 nm. The platelet concentrate received a low intensity flag. As shown in FIG. 8E, the unit clearly was contaminated but did not return a positive result on the BacT/ALERT® at any time point (days 1, 6, and 50).

Figure 9A:
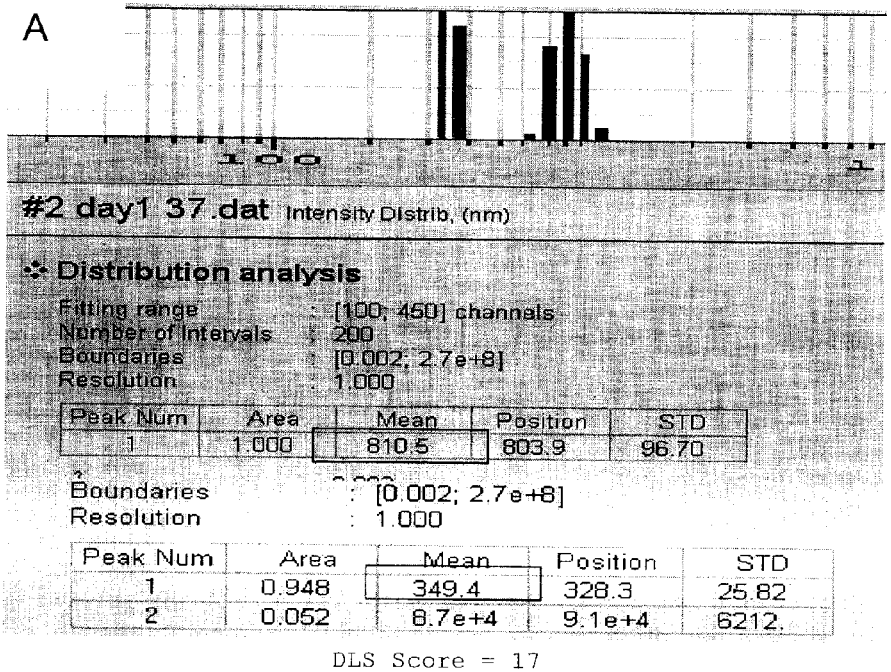
FIG. 9A show DLS bacterial detection on day 1 (after the manufacturing process)
Figure 9B:
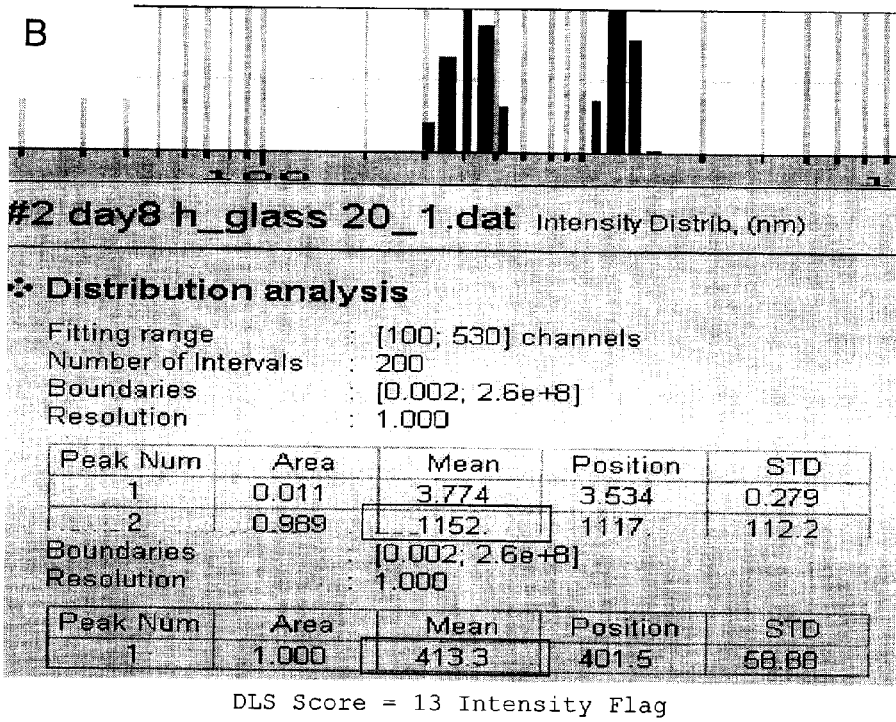
FIG. 9B show DLS bacterial verification on day 8.
Figure 9C:
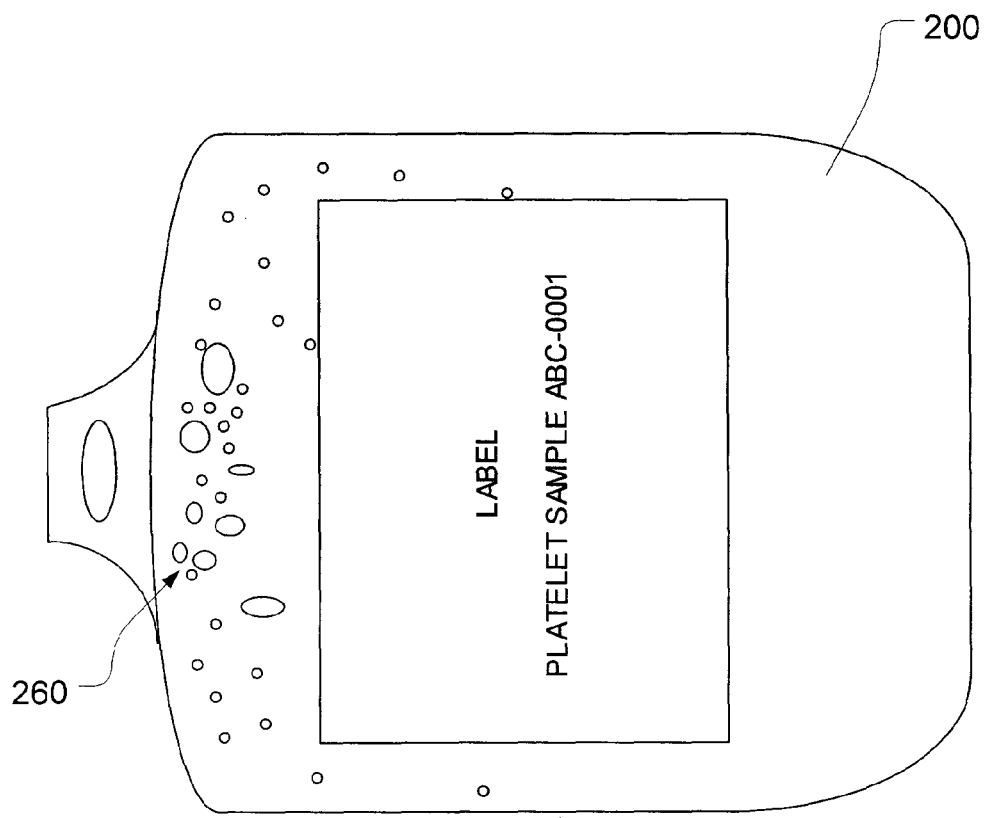
FIG. 9C is a schematic depiction based on a photograph of a platelet storage bag, showing massive bacterial growth on day 58.

FIGS. 9A and 9B show DLS bacterial detection on day 1 (after the manufacturing process) and verification on day 8. The respective DLS scores were 17 and 13. On day 8 the unit received a low intensity flag. In the distribution analysis presented in FIG. 9A, the size distributions of apheresis platelets and bacterial contamination on day 1 were measured at 37° C.: platelet radius 810±100 nm and bacterial radius 350±26 nm. In the distribution analysis presented in FIG. 9B, on day 8 of storage a mean platelet radius of 1150±110 nm, and a mean bacterial radius of 410±60 nm were measured at 20° C. As shown in FIG. 9C, visual inspection on day 58 indicated massive bacterial growth. The platelet concentrate was negative when analyzed by BacT/ALERT® on days 1, 6 and 18 of storage.

Figure 10:
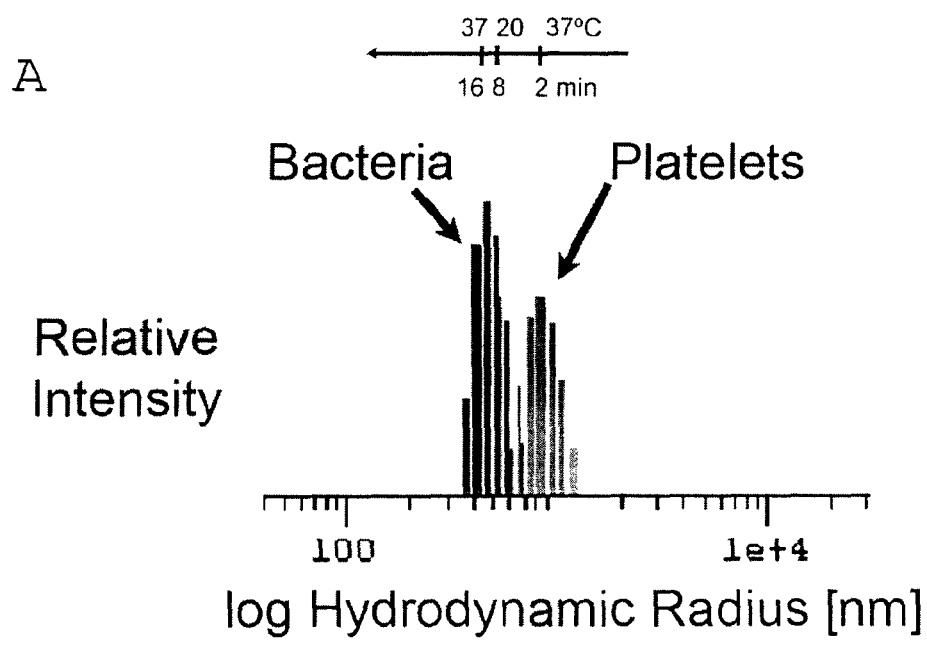
FIG. 10 illustrates how a low DLS score is derived from a bacterially contaminated platelet unit.

FIG. 10 illustrates how temperature response can be used to detect bacterial contamination. Platelets from a whole-blood-derived PRP unit undergo temperature-dependent shape change when cooled from 37° C. to 20° C. indicated by an increase in size. The temperature activation at 20° C. most likely led to a disappearance of the hydrodynamic radius of platelets of 850±194 nm at 37° C. due to the sedimentation of aggregates. Bacteria with a radius of 514±73 nm at 20° C. become prevalent. Bacteria do not respond to cooling. The size distribution analysis of bacteria resulted in a mean hydrodynamic radius of about 464±60 nm when the sample was re-warmed to 37° C. The temperature response is a characteristic of platelets and can therefore be used to differentiate between platelets and bacteria.

The foregoing thus provides a method of detecting bacteria by their size distribution determined from the dynamic light scattering (DLS) signal, and/or the negative effect on platelet quality, and/or the abnormally high or low total scattering intensity resulting in a low DLS score. The presence of bacteria in the sample causes a distinctive DLS signal (e.g. a recognizable peak in an expected range of particle size) that is distinct from other particles in a platelet concentrate (such as platelets, microparticles and proteins). Since the DLS signals are not affected by the type of bacterial metabolism (aerobic vs. anaerobic), it is believed that this technique can be utilized for virtually all species of bacteria. Furthermore, because multiple testing of the same platelet concentrate is possible, the speed of bacterial proliferation in the platelet concentrate becomes far less crucial. In addition to these advantages, the method and associated system are easy to use, provide quick and accurate results, and are believed to be more sensitive to bacterial contamination than prior-art techniques.

FIG. 11 provides examples for the use of the DLS score as an indicator of bacterial contamination. The DLS score can be obtained from a platelet concentrate within 15 minutes compared to several hours with the state-of-the-art BacT/ALERT culture method.

Although the DLS method is primarily intended as a technique for detecting bacterial contamination of a platelet concentrate, it can be applied to measuring bacterial contamination in other blood products, biological fluids or colloids.

It has turned out that it is not important to differentiate bacteria from other particles if the score is calculated. The presence AND/OR the effect of bacteria changes the score significantly. Thus, even when bacteria are not differentiated as separate particles their effect on platelets significantly reduces the score.

Identifying a specific species of bacteria in the Sample by correlating a mean particle size to a specific species of bacteria can be based on previously determined empirical data for the particular species of bacteria. For example, Applicant has developed sufficient empirical data regarding the species *Staphylococcus epidermidis* that this species can now be identified when a correlative mean particle size is observed.

DLS Scoring

DLS Scoring using the DLS system (e.g. the DLS-PM, or "Dynamic Light Scattering Platelet Monitor") can be done as follows:

$$DLS\ score = \left[\sum_{temp1}^{tempN} ((R_1 - SD_1) * I_1 - (R_2 - SD_2) * I_2)\right] \div 100$$

Where:
$R_1$=mean radius of particles with radius 500 nm-2500 nm (i.e. the "Platelet Size")
$SD_1$=standard deviation of the $R_1$ particle distribution (the narrower the distribution the better)
$I_1$=normalized intensity of the $R_1$ particle distribution (contribution of all particles totals 1)
$R_2$=particles 50 nm-499 nm in radius . . . microparticles
$SD_2$=standard deviation of the $R_2$ particle distribution (the narrower the distribution the better)
$I_2$=normalized intensity of the $R_2$ particle distribution (contribution of all particles totals 1) which is known herein as the "Relative Number of Microparticles"
$\Sigma$=sum over all temperatures 1 to N (e.g., 37_1, 20, 37_2) divided by 100, which is known herein as the "Temperature Response"

In a variant, an abbreviated score can be calculated by utilizing the DLS system illustrated in FIG. 5B along with the platelet storage bag depicted in FIG. 6B. In other words, this is the arrangement in which the sample holder 100 holds an entire bag between clamping members and DLS measurements are obtained through an optical access window in the wall of the bag. DLS scoring with this arrangement is performed at room temperature. While it is abbreviated, it is also less accurate.

From the foregoing explanation on DLS scoring, it should now be apparent that this formula combines all DLS parameters into one number or "score" and parallels the scoring scheme based on clinical outcome. IN the foregoing, "transfusion merit" is defined as the sum of the 1 h corrected count increment (CCI) and the 24 h CCI: transfusion merit score=1 h CCI+24 h CCI. In clinical practice, an acceptable 1 h CCI is 7 or higher and an acceptable 24 h CCI is 5 or higher. Thus, the minimum acceptable transfusion merit is 12.

In the table presented in FIG. 11, it is stated that a DLS score less than 12 would be unacceptable. The "sample quality" (i.e. quality of a given platelet concentrate) can thus be determined with reference to this DLS score. If the DLS score is less than 12, the unit would be discarded as being contaminated. If the DLS score is 12 or higher, then the concentrate is still considered useable or viable for transfusion or other uses. Persons of ordinary skill in the art will appreciate that this threshold score of 12 is an arbitrary cutoff (based on Applicant's correlation of the DLS score with other bacteria measurements and/or acceptable levels) and may be changed.

To summarize generally, and without limiting the foregoing, there are three basic indicators for bacterial contamination:

(1) A population of particles different from platelets, microparticles or proteins: This is depicted schematically in FIG. 12A. Direct DLS measurements using the DLS-PM (i.e. the system described herein) would show spikes at certain particle sizes that is therefore indicative of bacterial contamination. In other words, a method of detecting bacterial contamination in a sample of platelets can be accomplished by (a) obtaining DLS measurements on the sample of platelets by illuminating the sample with incident light and by collecting the scattered light; (b) determining a particle size distribution based on the scattered light; (c) identifying a cluster of particles on the particle size distribution that is distinct from a cluster of particles known to correspond to platelets; and (d) determining whether the sample is bacterially contaminated by the cluster of particles that are distinct from the cluster of particles corresponding to platelets. The DLS measurements can yield a particle size distribution, such as the one shown in FIG. 2. or the one shown in FIG. 7A. On the distribution, there may be one or more peaks (or "clusters") representing discrete and distinct populations of particles. One of those peaks represents the population of platelets. The presence or absence of further peaks or clusters representing other populations of particles (microparticles, bacteria, contaminants, etc.) can be used to determine that there is contamination of the tested sample.

(2) Bad quality platelets, i.e. low DLS score because of bacterial toxins or other direct effects of bacteria on platelets: This is depicted schematically in FIG. 12B. The bacterial toxins will cause activation of the platelets, resulting in an unduly high quantity of microparticles or other contaminants in the platelet sample. In other words, to avail oneself of this second indicator, a method of detecting bacterial contamination in a platelet sample would entail: (a) obtaining DLS measurements from the platelet sample; (b) determining whether a DLS score that is computed based on the DLS measurements is below a predetermined threshold; and (c) identifying the platelet sample as being bacterially contaminated when the DLS score is below the predetermined threshold. In one embodiment, the DLS score can be computed as:

$$DLS\ score = [(R_1 - SD_1) * I_1 - (R_2 - SD_2) * I_2] * 0.03$$

Where:
$R_1$=mean radius of particles with radius 500 nm-2500 nm (i.e. the "Platelet Size")
$SD_1$=standard deviation of the $R_1$ particle distribution (the narrower the distribution the better)
$I_1$=normalized intensity of the $R_1$ particle distribution (contribution of all particles totals 1)
$R_2$=particles 50 nm-499 nm in radius ("microparticles")
$SD_2$=standard deviation of the $R_2$ particle distribution (the narrower the distribution the better)
$I_2$=normalized intensity of the $R_2$ particle distribution (contribution of all particles totals 1) which is known herein as the "Relative Number of Microparticles"

3. Very high or very low scattering intensity: That is, if the intensity is doubled from what is expected of a platelet concentrate, the unit is flagged because the added scattering particles must be contaminants whereas, on the other hand, when platelets and bacteria aggregate they will settle out of the observation volume and the intensity will be very low. This is schematically depicted in FIG. 12C. If platelet aggregation occurs, then the light intensity will be low because the platelet-bacterium aggregation will tend to settle out of the observation volume, resulting in very little forward scatter or back scatter. On the other hand, if the scattering intensity is very high, this will mean that there is a very high quantity of contaminants or microparticles in the sample. In both cases, i.e. very low or very high, the sample is considered to be of bad quality and is thus to be discarded. To use this third indicator, a method of detecting bacterial contamination in a platelet sample would entail steps of: (a) obtaining DLS measurements from the platelet sample; (b) determining whether an intensity of scattered light from the DLS measurements is below a first predetermined intensity threshold or above a second predetermined intensity threshold; and (c) identifying the platelet sample as being bacterially contaminated when the DLS score is below the first predetermined intensity threshold or above the second predetermined intensity threshold.

For each of these three different bacterial contamination indicators, one of three different DLS instrument setups can be used (for a total of nine different combinations of indicators and DLS setups).

In a first DLS instrument setup, DLS measurements are obtained by placing a tube or capillary containing the sample into a sample holder of a DLS instrument. The sample holder has clamping members for holding and immobilizing the tube or capillary while providing multiple angles of optical access to the tube or capillary. The backing member and the clamping member provide optical access to the sample from many vantage points around the sample so as to enable collection of light at an angle oblique to light incident on the sample. In other words, the optical slots enable illumination of the sample from many different angles around the sample as well collection of scattered light from many different angles also.

In a second DLS instrument setup, a modified sample holder holds a modified platelet storage bag that includes an optical access window in a wall of a platelet storage bag. The DLS measurements are thus obtained through the optical access window retained between clamping members of the sample holder.

In a third DLS instrument setup, a sample of platelets is drawn into a tube (or tubing) appended to a platelet storage bag. The DLS measurements are then made on the volume of platelets within the tube. In one specific embodiment, the sample of platelets is drawn (or suctioned) into a detachable tube appended to the platelet storage bag by squeezing a filling bulb at the end of the tube. In this particular embodiment, the tube is then detached from the bag and placed between clamping members of the sample holder as if it were a standard capillary. Alternatively, DLS measurements can also be obtained on the sample in the tube without detaching it from the bag.

In yet another embodiment, the sample of platelets can be contained within a platelet storage bag having both an optical access window and a detachable tube appended to the bag. Where the bag has both an optical access window and a detachable tube, the end-user (clinician, technician, researcher, etc.) may choose to use either the access window for direct measurement in a modified sample holder (such as the one shown in FIG. 5B) or the detachable tube (which can be placed in a sample holder such as the one shown in FIGS. 3, 4 and 5A).

The embodiments of the invention described above are intended to be exemplary only. The scope of the invention is therefore intended to be limited solely by the scope of the appended claims.

The invention claimed is

1. A method for detecting bacteria in a sample, the method comprising:
   a) placing the sample in a dynamic light scattering (DLS) instrument;
   b) collecting DLS measurements from the sample by determining a relative intensity of scattered light and establishing a particle size distribution based on the DLS measurements, wherein the particle size distribution comprises at least distinct first and second populations of particles corresponding to first and second particles in the sample having different particle sizes, wherein said first population corresponds to platelets;
   c) comparing the first population to the second population and based upon said comparison,
   making determination that a quantity of bacteria is present in the sample when the second population exceeds a predetermined threshold; and
   d) if a determination has been made according to step c) that a quantity of bacteria is present in the sample, determining the quantity of bacteria present in the sample by comparison of the second population to the first population.

2. The method as claimed in claim 1 wherein each of the at least first and second distinct populations of particles in the particle size distribution is represented by a discrete peak, each peak corresponding to a different type of particle in the sample; and
   analyzing the discrete peaks
   and estimating a quantity of bacteria in the sample by analyzing the relative intensity of the scattered light for a discrete peak in the particle size distribution corresponding to the bacteria.

3. The method as claimed in claim 2 wherein the step of analyzing the discrete peaks further comprises identifying platelets, microparticles, proteins and bacteria by comparing mean particle sizes to expected particle size ranges for platelets, microparticles, proteins and bacteria, respectively, based on previously obtained empirical data.

4. The method as claimed in claim 1 further comprising a step of identifying a specific species of bacteria in the sample.

5. The method as claimed in claim 1 further comprising: controlling a temperature of said sample.

6. The method as claimed in claim 5 wherein said controlling said temperature of said sample comprises:
   incubating the sample at a temperature of either 37 degrees Celsius±2 degrees Celsius or 20 degrees Celsius±2 degrees Celsius.

7. The method as claimed in claim 5 wherein said controlling said temperature of said sample comprises:
   temperature cycling the sample between 37 and 20 degrees Celsius.

8. A method of detecting bacterial contamination in a platelet sample containing microparticles, the method comprising steps of:
   obtaining DLS measurements from the platelet sample, said DLS measurements being obtained while the temperature of said platelet sample is between 37 and 20 degrees Celsius±2 degrees Celsius;
   calculating a DLS score from the DLS measurements;
   determining whether the DLS score is below a predetermined threshold score; and
   identifying the platelet sample as being bacterially contaminated when the DLS score is below the predetermined threshold score.

9. A method of detecting bacterial contamination in a platelet sample, the method comprising steps of:
   obtaining DLS measurements from the platelet sample; said DLS measurements comprising a total scattering intensity derived from scattering intensities from plural distinct populations of particles in the sample, wherein each of said plural distinct populations is associated with an intensity of scattered light and wherein one of said plural distinct populations correspond to platelets in the sample and the other plural distinct populations correspond to other microparticles in the sample;

determining whether an intensity of scattered light from one of said other plural distinct populations is below a first predetermined intensity threshold;

determining whether the total scattering intensity is above a second predetermined intensity threshold and identifying the platelet sample as being bacterially contaminated when the intensity of scattered light from said one of said other plural distinct populations is below the first predetermined intensity threshold or when the total scattering intensity is above the second predetermined intensity threshold.

10. A method of detecting bacterial contamination in a sample of platelets, the method comprising steps of:

obtaining DLS measurements on the sample of platelets by illuminating the sample with incident light and by collecting the scattered light;

establishing a single particle size distribution based on the scattered light, said single particle size distribution comprising plural data sets from the DLS measurements and wherein each data set corresponds to a cluster of particles in the sample that is distinct from other particles in the sample;

identifying a first data set from the plural data sets that corresponds to a cluster of particles known to correspond to platelets; identifying a second data set from the plural data sets that correspond to a cluster of particles on the particle size distribution that is distinct from the first data set;

comparing the first data set to the second data set and if the second data set exceeds a predetermined threshold value, making a determination that the second data set corresponds to bacteria; and when a determination has been made that the second data set corresponds to bacteria, estimating the quantity of bacteria in the sample by comparing the first and second data sets.

* * * * *